United States Patent
Yam et al.

(10) Patent No.: US 9,708,528 B2
(45) Date of Patent: Jul. 18, 2017

(54) ROBUST PHOTOCHROMIC COMPOUNDS WITH SILICON- OR PHOSPHORUS-CONTAINING HETEROCYCLIC RING AND THE PRODUCTION THEREOF

(71) Applicant: THE UNIVERSITY OF HONG KONG, Hong Kong (HK)

(72) Inventors: Vivian Wing-Wah Yam, Hong Kong (HK); Jacky Chi-Hung Chan, Hong Kong (HK); Hok-Lai Wong, Hong Kong (HK); Nathan Man-Wai Wu, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 26 days.

(21) Appl. No.: 14/734,233

(22) Filed: Jun. 9, 2015

(65) Prior Publication Data
US 2015/0361332 A1    Dec. 17, 2015

Related U.S. Application Data

(60) Provisional application No. 62/011,797, filed on Jun. 13, 2014.

(51) Int. Cl.
*C07F 7/02* (2006.01)
*C09K 9/02* (2006.01)
*C07F 7/08* (2006.01)
*C07F 9/6568* (2006.01)

(52) U.S. Cl.
CPC .............. *C09K 9/02* (2013.01); *C07F 7/0814* (2013.01); *C07F 7/0827* (2013.01); *C07F 9/65685* (2013.01); *C07F 9/65686* (2013.01); *C07F 9/65688* (2013.01); *C09K 2211/1029* (2013.01); *C09K 2211/1033* (2013.01); *C09K 2211/1037* (2013.01); *C09K 2211/1092* (2013.01); *C09K 2211/1096* (2013.01)

(58) Field of Classification Search
CPC ............. C09K 9/02; C07F 9/6569; C07F 7/08
USPC ......................................................... 556/400
See application file for complete search history.

(56) References Cited

U.S. PATENT DOCUMENTS

| | | |
|---|---|---|
| 5,175,079 A | 12/1992 | Van et al. |
| 5,183,726 A | 2/1993 | Taniguchi et al. |
| 5,443,940 A | 8/1995 | Tatezono et al. |
| 5,622,812 A | 4/1997 | Tatezono et al. |
| 6,359,150 B1 | 3/2002 | Fukudome et al. |
| 6,479,604 B1 | 11/2002 | Kim et al. |
| 2003/0086978 A1 | 5/2003 | Kim et al. |
| 2003/0130456 A1 | 7/2003 | Kim et al. |
| 2007/0082977 A1 | 4/2007 | Shibahashi et al. |

FOREIGN PATENT DOCUMENTS

| | | |
|---|---|---|
| WO | 2007-105699 | 9/2007 |
| WO | 2013-044371 | 4/2013 |

OTHER PUBLICATIONS

CAS Registry of the Amer. Chem. Soc., Registry No. 1271102-02-3 (Mar. 28, 2011).*
Tamao et al., Journal of the Amer. Chem. Soc. (1996), 118(47), 11974-11975.*
Cipolloni et al., Journal of Physical Chem. (2008), 112, 4765-4771.*
Yamaguchi et al., Tetrahedron Letters (2011), 52(43), 5601-5604.*

* cited by examiner

*Primary Examiner* — Porfirio Nazario Gonzalez
*Assistant Examiner* — Kofi Adzamli
(74) *Attorney, Agent, or Firm* — Amin, Turocy & Watson, LLP

(57) ABSTRACT

In one embodiment, provided are a new class of diarylethene-containing photochromic compounds with the incorporation of silicon- or phosphorus-containing heterocycles into the "ethene" part of the diarylethene backbone that has been shown to be capable of displaying tunable, robust and thermally stable photochromic properties. Also provided are methods for synthesizing these compounds, as well as uses of these compounds as these compounds may be used as the photochromic layer in an optical recording material and other optical functioning devices.

17 Claims, 6 Drawing Sheets

ROBUST PHOTOCHROMIC COMPOUNDS WITH SILICON- OR PHOSPHORUS-CONTAINING HETEROCYCLIC RING AND THE PRODUCTION THEREOF

CROSS REFERENCE TO RELATED APPLICATION

This application claims priority to provisional application Ser. No. 62/011,797, filed on Jun. 13, 2014, which is incorporated herein by reference.

TECHNICAL FIELD

Described herein relates to the design of novel photochromic heterocyclic compounds and their photochromic studies. The design of these photochromic compounds is based on the cis-diarylethene structure, which forms part of the mono- or poly-heterocyclic compounds that contain a silicon- or a phosphorus-containing heterocyclic ring. These compounds can be used as the photochromic layer in an optical recording material and other optical functioning devices.

BACKGROUND

Photochromism is defined as "a reversible transformation of a single chemical species being induced in one or both directions by absorption of electromagnetic radiation, with two states having different distinguishable absorption spectra". Photochromic compounds are compounds that possess at least two isomeric forms, which have different physical properties, such as absorption and emission properties, refractivity, and the like, and can be transformed from one form to another by photo-excitations at prescribed wavelengths.

Photochromism has been extensively studied due to its potential use for optical recording and other optical functioning devices. To be practically used as optical recording materials, both isomeric forms must be thermally stable and possess excellent durability for reversible photochromic reactivity. Diarylethene is one class of photochromic compounds, which possesses all these necessary properties, and therefore is a suitable class of compounds for the construction of optical functioning devices. The cis-configuration of both aryl groups in the diarylethenes studied is generally fixed by an upper cycloalkane structure, such as fluorinated alicyclic group, aromatic group, anhydride and maleimide group. Apart from the difference in absorption characteristics and the like between the two forms and their thermal stabilities, the availability of desirable excitation wavelengths that can be tuned and selected for the photochromic reactions also represents an important aspect in the design of materials for optical functioning devices.

Even though there has been increasing interest in diarylethene-containing photochromic materials, most efforts have been focused on the derivatization of the diarylperfluorocyclopentenes to tune the photophysical and photochromic behaviors while less efforts have been made in the design and synthesis of different types of diarylethenes with excellent photochromic properties. However, the derivatization of diarylperfluorocyclopentenes has been rather limited with most of the works mainly focused on modifications at the substituted aryl groups only.

The most commonly studied heterocycles include pyrroles, thiophenes, indoles, thiazoles, imidazoles and others. Amongst the many heterocycles, phospholes and siloles have been less extensively studied, but have recently attracted increasing interests due to their unusual electronic and optical properties and possible application as organic light-emitting devices (OLEDs). Recently, Yam and co-workers [Yam, V. W.-W.; Ko, C.-C.; Zhu, N. J. Am. Chem. Soc. 126, 12734 (2004); Yam, V. W.-W.; Lee, J. K.-W.; Ko, C.-C. Zhu, N. J. Am. Chem. Soc. 131, 912 (2009); Wong, H.-L.; Ko, C.-C.; Lam, W. H.; Zhu, N.; Yam, V. W.-W. Chem. Eur. J. 15, 10005 (2009); Poon, C.-T.; Lam, W. H.; Yam, V. W.-W. J. Am. Chem. Soc. 133, 19622 (2011)] and other research groups [Nakashima, T.; Fujii, R.; Kawai, T. Chem. Eur. J. 17, 10951 (2011); Kühni, J.; Belser, P. Org. Lett. 9, 1915 (2007)] have shown that the incorporation of heterocycles into the "ethene" part of the diarylethene backbone, instead of derivatizing the pendants of the bis (thienyl)perfluorocyclopentene core, can enrich the photochromic and photophysical behaviors. In spite of the increasing interest in the use of phospholes and siloles and their derivatives for the fabrication of OLEDs, there are no examples on the use of functionalized phosphole and silole as the "ethene" part of the photochromic diarylethene backbone.

Further information can be found in U.S. Pat. Nos. 5,175,079, 5,183,726, 5,443,940, 5,622,812, and 6,359,150; Japanese patents JP 2-250877, JP 3-014538, JP 3-261762, JP 3-261781, JP 3-271286, JP 4-282378, JP 5-059025, JP 5-222035, JP 5-222036, JP 5-222037, JP6-199846, JP 10-045732, JP 2000-072768, JP 2000-344693, JP 2001-048875, JP 2002-226477, JP 2002-265468 and JP 2002-293784; and in Irie, M.; Mohri, M., J. Org. Chem. 53. 803 (1988); Nakamura, S.; Irie, M. J. Org. Chem. 53. 6136 (1988); and Irie, M. Chem. Rev. 100. 1685 (2000).

SUMMARY

The invention includes the use of mono- or poly-heterocyclic compounds to perturb the properties of the diarylethenes in the photochromic compounds. Described below is a report of the design, synthesis and studies of cis-diarylethene-containing compounds, with the incorporation of silicon- or phosphorus-containing heterocycles into the "ethene" part of the diarylethene backbone. The photophysical properties show the advantageous use as tunable, robust and thermally stable photochromic materials.

One consequence is to provide a new class of diarylethene-containing photochromic compounds with the incorporation of silicon- or phosphorus-containing heterocycles into the "ethene" part of the diarylethene backbone that has been shown to be capable of displaying tunable, robust and thermally stable photochromic properties.

Described herein are a new class of silicon- or phosphorus-containing heterocyclic compounds of the formula:

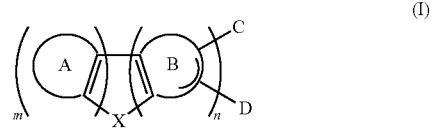

(I)

wherein X refers to heteroatoms including one or more of silicon or phosphorus, A and B are cyclic structure derivatives, m and n are the number of rings in the cyclic structure derivatives and m and n are independently greater than or equal to zero; C and D are heterocyclic groups, provided that C and D are cyclizable by irradiation with light to form cyclohexadiene ring for tuning the optical properties.

Also described herein is an optical recording material containing a recording layer comprising of a photochromic substance that is capable of reversibly undergoing a color change in such a manner that when photoirradiated with UV light, the photochromic substance undergoes a color change and when irradiated with visible light or near-infrared radiation, the photochromic substance returns to the initial color, in which information is recorded by irradiating the recording layer with light, wherein the photochromic substance is a diarylethene-containing heterocycle derivatives of the formula (I) as defined above.

DETAILED DESCRIPTION

Figure 1:
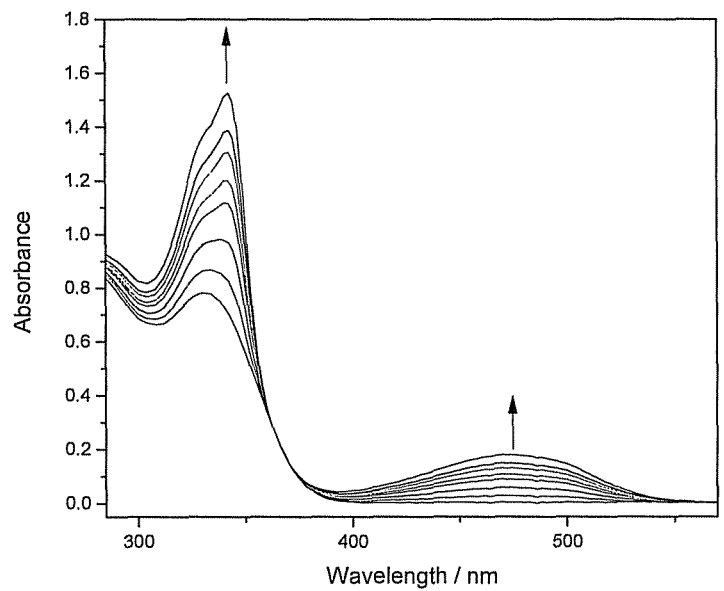
FIG. 1 shows the UV-vis absorption spectral changes of 1 in degassed benzene upon excitation at 362 mm.

Embodiments are directed to a new class of diarylethene-containing photochromic compounds with the incorporation of silicon- or phosphorus-containing heterocycles into the "ethene" part of the diarylethene backbone. The compounds have the chemical structure shown in generic formula (I):

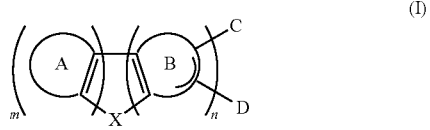

(I)

wherein X refers to heteroatoms including one or more of silicon or phosphorus, A and B are cyclic structure derivatives, m and n are the number of rings in the cyclic structure derivatives and they are independently greater than or equal to zero; C and D are heterocyclic groups, provided that C and D are cyclizable by irradiation with light to form cyclohexadiene ring for tuning the optical properties.

Heterocyclic ring with X refers to the silicon- or phosphorus-containing heterocycles, wherein X includes, but not limited to, SiRR', P(O)R, P(BH$_3$)R, P(BL$_3$)R, P(S)R, P(Se)R, P(CH$_3$)R, P(SR')R, PR, P(R')R, P(WL$_5$)R, P(CrL$_5$)R, P(MnL$_5$)R, P(MoL$_5$)R, P(ReL$_5$)R, P(PtL$_3$)R, P(PdL$_3$)R, P(CuL$_3$)R, P(CuL)R, P(RuL$_5$)R, P(IrL$_5$)R, P(FeL$_4$)R, P(RhL$_3$)R, P(RhL$_5$)R, P(CoL$_3$)R, P(NiL$_3$)R, P(AgL)R, P(AgL$_3$)R, P(AuL)R, or P(AuL)R' where R, R' or L is independently alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group, wherein X refers to P(CH$_3$)R or P(R')R, and wherein P(CH$_3$)R or P(R')R can be having a counter-anion: OTf$^-$, PF$_6^-$, BPh$_4^-$, ClO$_4^-$ or halide ions, where R and R' are independently alkyl, alkenyl, alkylaryl, cycloallcyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

In any R group or hydrocarbyl group (such as alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group, for example), such group can contain 1 to 50 carbon atoms. In another embodiment, any R group or hydrocarbyl group contains 1 to 25 carbon atoms.

Rings A and B are cyclic structure derivatives where the cyclic structures are independently selected from a 5- or 6-membered arene, heteroacene or heterocycle known in the art. The arene, heteroacene or heterocycle can be benzene, pyridine, thiophene, furan, pyrazole, imidazole, oxazole, isoxazole, thiazole, isothiazole, isoquiolione, pyrrole, pyrazine, pyridazine, pyrimidine, benzimidazole, benzofuran, benzothiazole, indole, naphthalene, anthracene, pyrene, triazole, tetrazole, pyran, thiapyran, oxadiazole, triazine, tetrazine, carbazole, dibenzothiophene, dibenzofuran, fluorene and derivatives thereof.

Rings A and B can be unsubstituted or can be substituted with one or more alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group, and additionally, or alternatively, any two adjacent substituted positions of rings A and B together form, independently, a fused 5- or 6-membered cyclic group, wherein the said cyclic group is cycloalkyl, cycloheteroalkyl, aryl, or heteroaryl, and wherein the fused 5- to 6-membered cyclic group may be substituted with one or more of alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

Specific examples of the diarylethene-containing photochromic compounds of formula (I) include the following.

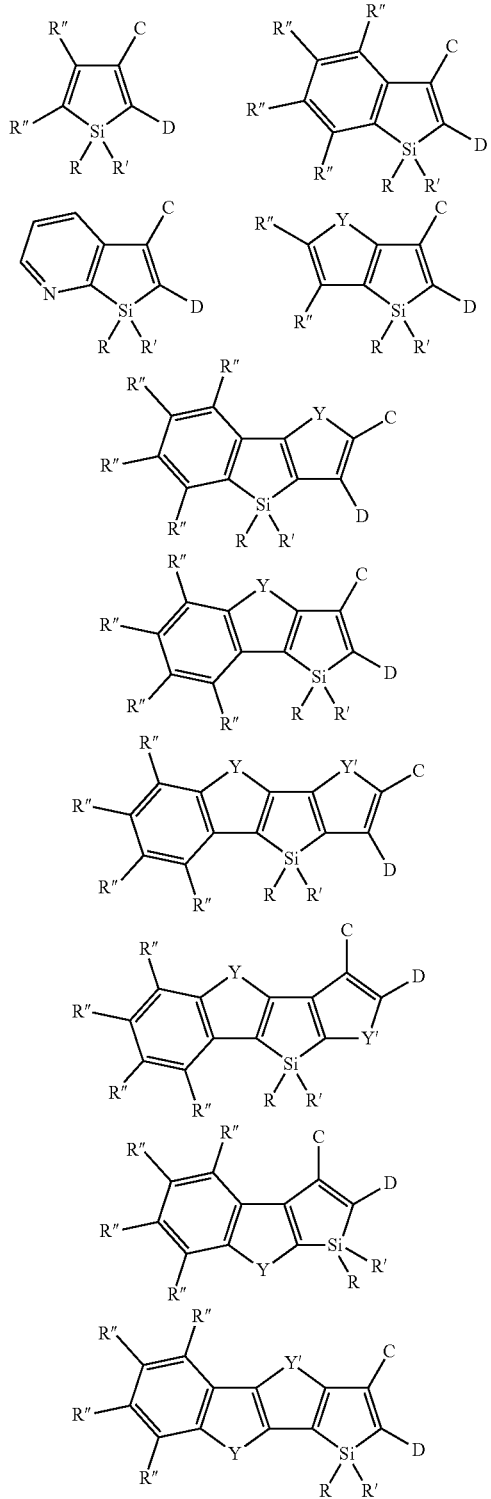

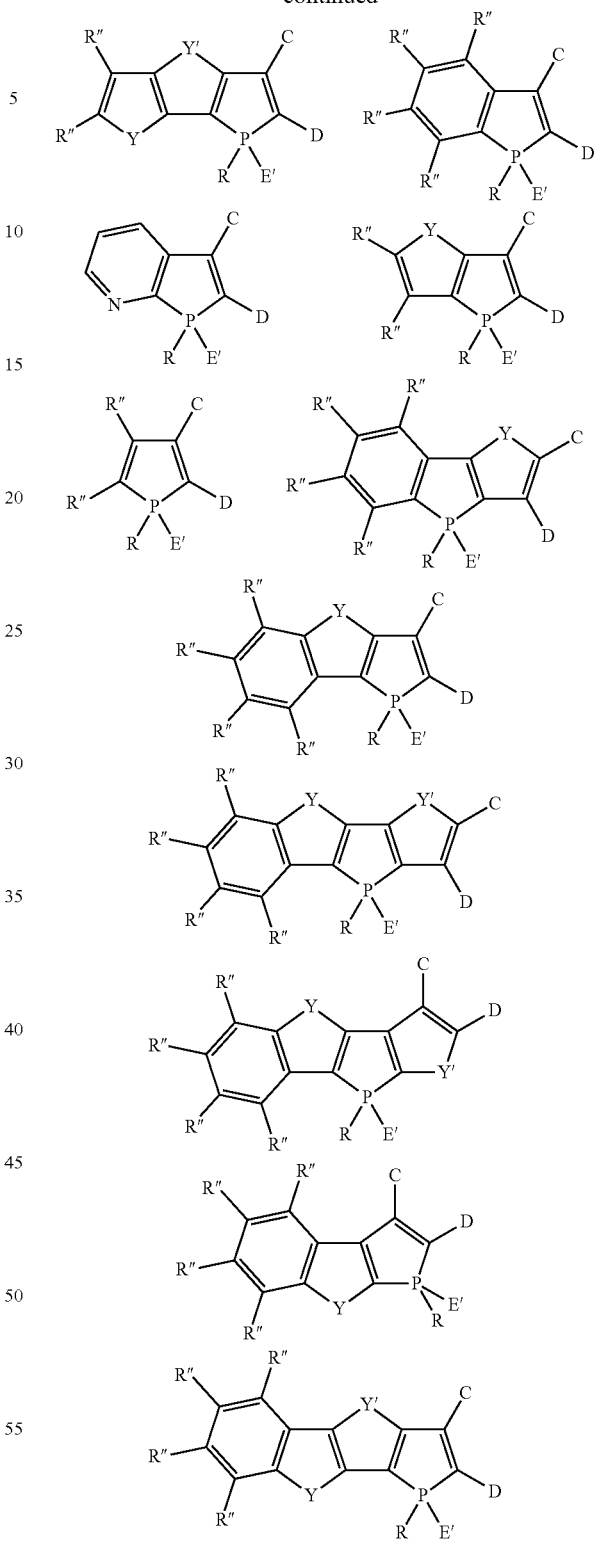

-continued

In the above formulae (I), the R, R' and R" may be alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

Y and Y' are heteroatoms, such as —S, $SO_2$, O, Se and NR. P-E' group can be P(=O), P(=S), P($BH_3$), P($CH_3$), P(lp), P(R'), P($BL_3$), P($WL_5$), P($CrL_5$), P($MnL_5$), P($MoL_5$), P($ReL_5$), P($PtL_3$), P($PdL_3$), P($CuL_3$), P(CuL), P($RuL_5$), P($IrL_5$), P($FeL_4$), P($RhL_3$), P($RhL_5$), P($CoL_3$), P($NiL_3$), P(AgL), P($AgL_3$), P(AuL), or P(AuL)', where lp is lone pair electron and R, R' or L is independently alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group, wherein the said P-E' group is P($CH_3$) or P(R'), and wherein P($CH_3$) or P(R') may be having a counter-anion: $OTf^-$, $PF_6^-$, $BF_4^-$, $BPh_4^-$, $ClO_4^-$ or halide ions, where R' is independently alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

The diarylethene-containing heterocycle derivatives of the present invention have the formula (I) as defined above. In the present invention, the heterocyclic group for C and D has the formula (II) or (III):

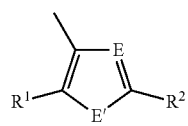

(II)

wherein

E may be C—$R^3$ or N;

E' may be heteroatoms, such as —S, $SO_2$, O, Se and $NR^4$;

$R^1$ is an alkyl group, alkoxy group, halogen atom or trifluoromethyl group. $R^2$ and $R^3$ independently represent atoms or groups selected from the group of hydrogen atom, halogen atom, hydroxyl group, alkyl group, alkynyl group, alkoxy group, cyano group, nitro group, alkylcarbonyl group, alkoxycarbonyl group, perfluoroallyl group, aryl group, cycloalkyl group, arylcarbonyl group, aryloxycarbonyl group, diarylamino group, dialkylamino group, mono- or dialkylaminocarbonyl group, alkylcarbonyloxy group, arylcarbonyloxy group, aryloxy group, alkoxycarbonyl group, and aryloxycarbonyloxy group. $R^4$ is a hydrogen atom or a substituted or unsubstituted alkyl, aryl or cycloalkyl group.

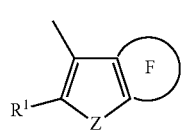

(III)

wherein

Z may be heteroatoms, such as —S, $SO_2$, O, Se and $NR^4$;

$R^1$ is an alkyl group, alkoxy group, halogen atom or trifluoromethyl group. $R^4$ is a hydrogen atom or a substituted or unsubstituted alkyl, aryl or cycloalkyl group.

Ring F is cyclic structure derivatives where the cyclic structures are independently selected from a 5- or 6-membered arene, heteroacene or heterocycle known in the art. The arene, heteroacene or heterocycle can be benzene, pyridine, thiophene, furan, pyrazole, imidazole, oxazole, isoxazole, thiazole, isothiazole, isoquioline, pyrrole, pyrazine, pyridazine, pyrimidine, benzimidazole, benzofuran, benzothiazole, indole, naphthalene, anthracene, pyrene, triazole, tetrazole, pyran, thiapyran, oxadiazole, triazine, tetrazine, carbazole, dibenzothiophene, dibenzofuran, fluorene and derivatives thereof.

Ring F can be unsubstituted or can be substituted with one or more alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group, and additionally, or alternatively, any two adjacent substituted positions of ring F together form, independently, a fused 5- or 6-membered cyclic group, wherein the said cyclic group is cycloalkyl, cycloheteroalkyl, aryl, or heteroaryl, and wherein the fused 5- to 6-membered cyclic group may be substituted with one or more of alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

Specific examples of formula (II) and (III) include the following.

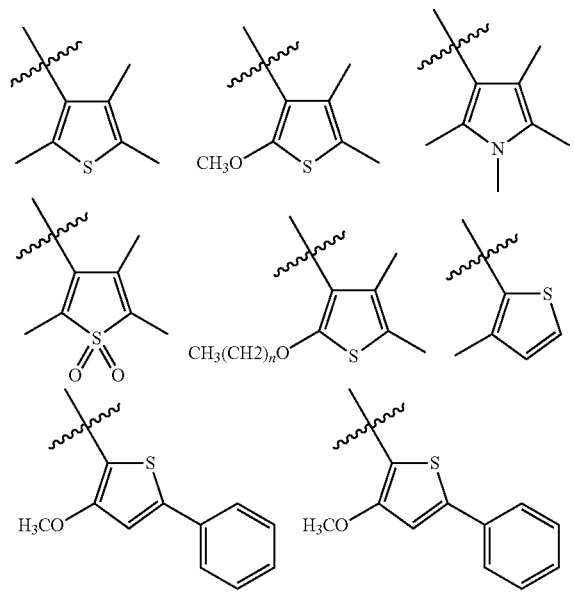

-continued
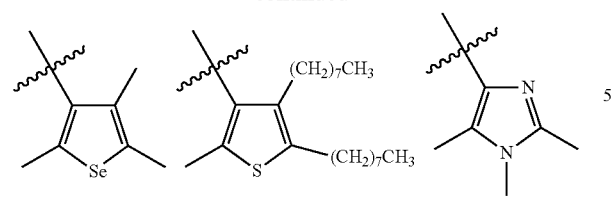
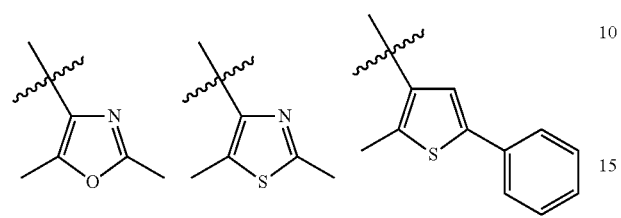
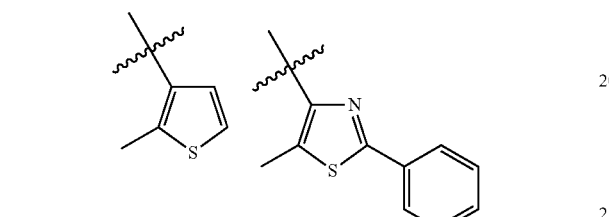
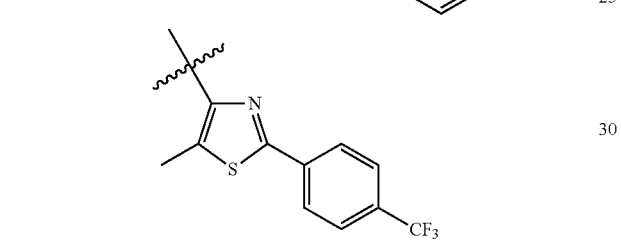
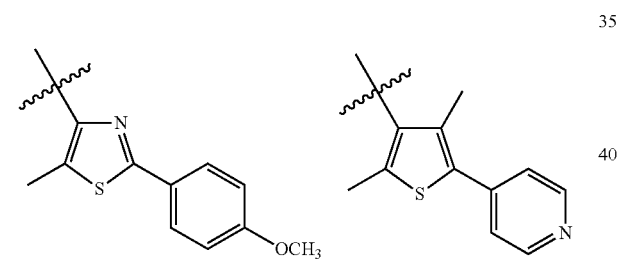
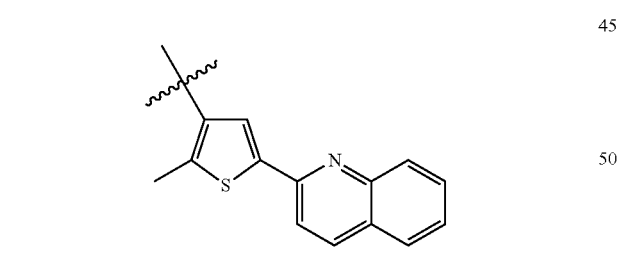
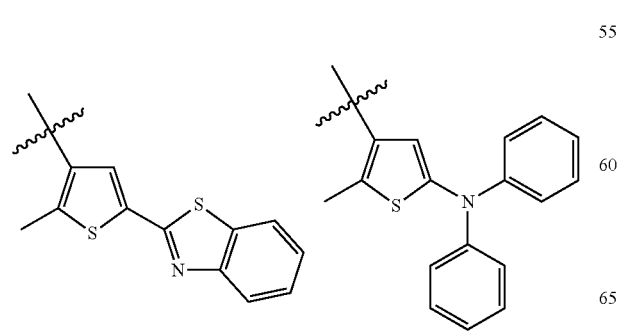
-continued
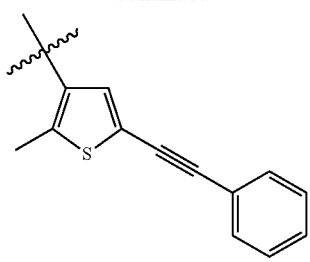
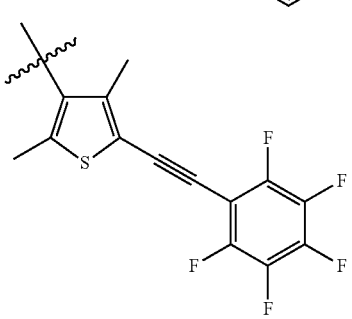
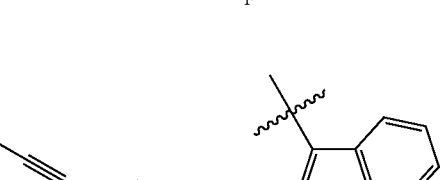
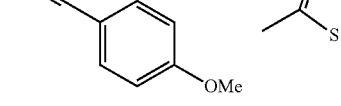
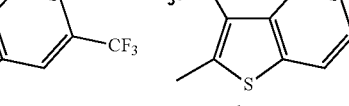
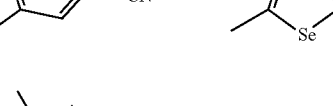
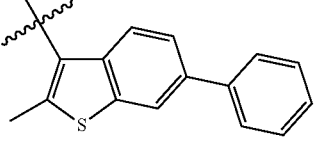

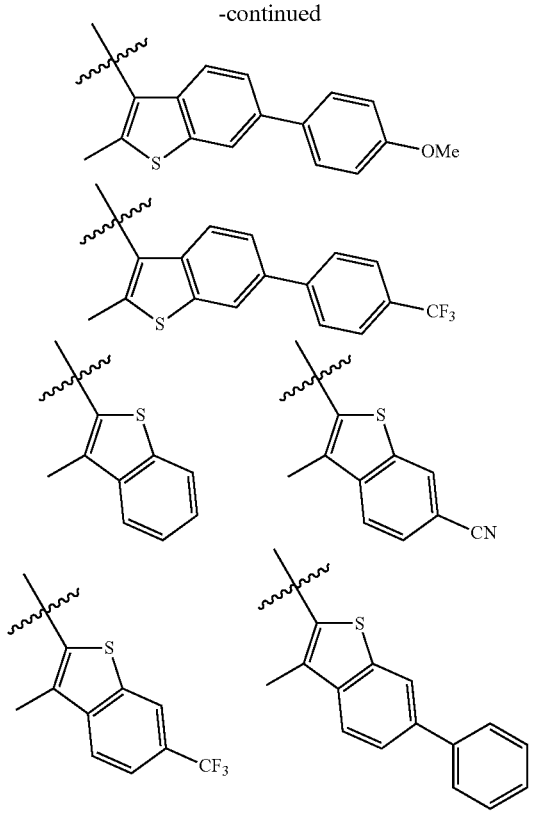

The term "halo" or "halogen" includes a fluorine, chlorine, bromine and iodine. The term "alkyl" as used herein includes either a straight or branched chain alkyl groups. The alkyl groups contain at least one to eighteen or more carbon atoms, including, but not limited to, methyl, ethyl, propyl, isopropyl, butyl, isobutyl, tert-butyl, 3-ethylhexyl and the like. In addition, the alkyl group may be unsubstituted or substituted with one or more substituents including alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

The term "alkenyl" as used herein includes both straight and branched chain alkene radicals of two to eighteen or more carbon atoms. The alkenyl group can be unsubstituted or substituted with one or more substituents including, but not limited to, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

The term "alkynyl" as used herein includes both straight and branched chain alkyne radicals of two to eighteen or more carbon atoms. The alkynyl group can be unsubstituted or substituted with one or more substituents including, but not limited to, alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

The term "arylalkynyl" as used herein includes an alkynyl group which has an aromatic group as a substituent. The arylalkynyl group may be unsubstituted or substituted with one or more substituents including, but not limited to, alkyl, alkenyl, alkynyl, alkyl aryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

The term "alkylaryl" as used herein includes an alkyl group which has an aromatic group as a substituent. The alkynyl group may be unsubstituted or substituted with one or more substituents including, but not limited to, alkyl, alkenyl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

The term "cycloalkyl" as used herein includes cyclic alkyl groups. Cycloalkyl groups can contain 3 to 7 or more carbon atoms and include cyclopropyl, cyclopentyl, cyclohexyl, and the like. Cycloalkyl groups may be unsubstituted or substituted with one or more substituents including, but not limited to, alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

The term "alkoxy" as used herein includes linear or branched alkoxy groups of one to eighteen or more carbon atoms, and can be unsubstituted or substituted with one or more substituents including, but not limited to, alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

Aryl alone or in combination includes carbocyclic aromatic systems containing one, two or three rings, wherein each ring may be attached together in a pendant manner or may be fused and can be 5- or 6-membered rings. The aryl rings can be unsubstituted or substituted with one or more substituents including, but not limited to, alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

Heteroaryl alone or in combination includes heterocyclic aromatic systems which contain one, two, three or more rings, wherein each ring may be combined in a pendant or fused manner, wherein each ring of the system is a 5- or 6-membered rings.

Heterocyclic and heterocycles refer to a 3- to 7-membered ring containing at least one heteroatom. The heterocyclic rings can be aromatic, including, but not limited to, pyridine, thiophene, furan, pyrazole, imidazole, oxazole, isoxazole, thiazole, isothiazole, isoquinoline, pyrrole, pyrazine, pyridazine, pyrimidine, benzimidazole, benzofuran, benzothiazole, indole, naphthalene, triazole, tetrazole, pyran, thiapyran, oxadiazole, triazine, carbazole, dibenzothiophene, dibenzofuran, indole, and fluorene. The heterocyclic rings can be non-aromatic, including, but not limited to, aziridine, oxirane, thiirane, oxaziridine, dioxirane, azetidine, oxetane, thietane, diazetidine, dioxetane, dithietane, tetrahydrofurane, thiolane, borolane, phospholane, arsolane, stibolane, bismolane, silane, stannolane, piperazine, piperidine, and pyrrolidine. Heterocyclic rings can be unsubstituted or substituted, which can include, but are not limited to, alkyl, alkoxy, aryl. The heteroatoms include, but not limited to, S, O, N, Si or P.

The present invention is illustrated by the following non-limiting examples. It is to be understood that changes and variations can be made therein without deviating from the scope and the spirit of the invention as hereinafter claimed. It is also understood that various theories as to why the invention works are not intended to be limiting. The compounds described herein are represented throughout by their monomeric structure. As is well known to those in the art, the compounds may also be present as dimers, trimers, larger oligomers or dendrimers.

In some embodiments, the photochromic compounds of formula (I) are prepared in high purity. High purity means one of at least 90% by weight pure, at least 95% by weight pure, at least 99% by weight pure, or at least 99.9% by weight pure. The silicon- or phosphorus-containing heterocyclic ring structure can be prepared by any method known to those skilled in the art, for example the intermolecular coupling reaction of 2-silylaryl bromides with alkynes disclosed in Liang, Y.; Geng, W.; Wei, J.; Xi, Z., *Angew. Chem. Int. Ed.* 51, 1934 (2012) for preparing the silicon-containing hetetocycles, the intramolecular dehydrogenative cyclization disclosed in Kuninobu, Y.; Yoshida, T.; Takai, K. *J. Org. Chem.* 76, 7370 (2011) and the silver-mediated dehydrogenative annulation disclosed in Unoh, Y.; Hirano, K.; Satoh, T.; Miura, M. *Angew. Chem. Int. Ed.* 52, 12975 (2013) for the phosphorus-containing heterocycles, which are incorporated herein by reference. The photochromic diarylethene functional moiety was introduced by using their corresponding intermediates, for example 1,2-diarylethyne for the intramolecular coupling reaction with 2-silylaryl bromides for the formation of silicon-containing heterocycles, cis-diarylethene-containing hydrophosphine oxide for the intramolecular dehydrogenative cyclization and 1,2-diarylethyne for the silver-mediated dehydrogenative annulation for the formation of phosphorus-containing heterocycles, to yield the target photochromic compounds. The phosphorus center in phosphole oxides was subsequently functionalized by various chemical modifications, such as oxidation to phosphine oxides, sulfides or selenides, formation of phosphonium salts, or complexation with Lewis acids or transition metals.

On the other hand, described herein is an optical recording material having such a silole- or phosphole-containing photochromic compound incorporated in a recording layer, wherein information recording is conducted by inducing a color change when irradiated with light and the reproduction of the recorded information is affected by reading the difference in the absorbance or in the reflectivity between the portion where such color changes have occurred and the portion where no such color change has occurred. The optical recording material can be prepared by forming a recording layer by any method known to those skilled in the art, for example by the following method:

The photochromic compound is dissolved in a solvent such as dichloromethane, chloroform, carbon tetrachloride, benzene or cyclohexane, if necessary, together with a binder such as poly(methyl methacrylate) (PMMA), polyester resin, polystyrene resin, polyvinyl butyral resin or polyvinylidene chloride, and then, coated on a suitable substrate including, but not limited to, quartz plate, glass plate and plastic film by spin-coating, spray-coating, dip-coating, layer-by-layer deposition, or ink-jet printing, or vapor deposition.

The following examples illustrate the subject invention. Unless otherwise indicated in the following examples and elsewhere in the specification and claims, all parts and percentages are by weight, all temperatures are in degrees Centigrade, and pressure is at or near atmospheric pressure.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

Example 1

Compounds 1-5 were prepared according to the methodology as illustrated in Scheme 1 below. Compounds 6-8 were prepared using the methodology shown in Scheme 2, whereas compounds 9-10 were prepared according to Scheme 3 and compound 11 was prepared according to Scheme 4. 1,2-Bis(2,5-dimethylthiophen-3-yl)ethyne was prepared in four steps from 2,5-dimethylthiophene, as shown in Scheme 1. Then the target compounds 1-10 were prepared using similar methodology as a literature procedure for the intermolecular coupling reaction of 2-silylaryl bromides with alkynes disclosed in Liang, Y.; Geng, W.; Wei, J.; Xi, Z., *Angew. Chem. Int. Ed.* 51, 1934 (2012), which is incorporated herein by reference. Compound 11 was prepared using the similar procedure as other derivatives, except an excess of 1,2-bis(2,5-dimethylthiophen-3-yl) ethyne was used (~3 times). Compounds 12-16 were prepared according to the following methodology as illustrated in Scheme 5 below. Compounds 17-20 were prepared using the methodology shown in Scheme 6, whereas compounds 21-22 were prepared according to Scheme 7. The phosphole oxides were prepared using similar methodology as a literature procedure for the intramolecular dehydrogenative cyclization disclosed in Kuninobu, Y.; Yoshida, T.; Takai, K. *J. Org. Chem.* 76, 7370 (2011), which is incorporated herein by reference. As indicated in Scheme 6 and Scheme 7, the phosphorus center in phosphole oxides was further functionalized by various chemical modifications, for example the methods disclosed in Hay, C.; Fischmeister, C.; Hissler, M.; Toupet, L.; Réau, R. *Angew. Chem., Int. Ed.* 39, 1812 (2000) and Dienes, Y.; Durben, S.; Kárpáti, T.; Neumann, T.;

Englert, U.; Nyulászi, L.; Baumgartner, T. *Chem. Eur. J.,* 13, 7487 (2007), which are incorporated herein by reference. Compounds 23-28 were prepared according to the methodology as depicted in Scheme 8. Compounds 29-32 were prepared by the methodology described in Scheme 9. Compounds 33 was prepared according to the methodology as shown in Scheme 10. The phosphole oxides were prepared using similar methodology as the literature procedure for the silver-mediated dehydrogenative annulation disclosed in Unoh, Y.; Hirano, K.; Satoh, T.; Miura, M. *Angew. Chem. Int. Ed.* 52, 12975 (2013) and Chen, Y.-R.; Duan, W.-L. *J. Am. Chem. Soc.* 135, 16754 (2013), which are incorporated herein by reference. The functionalization at the phosphorus center of the phosphole to afford compounds 29-32 was achieved by various chemical modifications, which were disclosed by Chan, J. C.-H.; Lam, W. H.; Wong, H.-L.; Wong, W.-T.; Yam. V. W.-W. *Angew. Chem. Int. Ed.* 52, 1 (2013), Bouit P.-A.; Escande, A.; Szücs, R.; Szieberth, D.; Lescop, C.; Nyulászi, L.; Hissler, M.; Réau, R. *J. Am. Chem. Soc.* 134, 6524 (2012) and Moussa, M. E. S.; Friess, F.; Shen, W.; Hissler, M.; Réau, R.; Lescop, C. *Chem. Commun.* 49, 6158 (2013), which are incorporated herein by reference. The phosphole-containing metal complex 33 was prepared using similar methodology as the literature procedure reported in Dienes, Y.; Eggenstsin, M.; Kárpáti, T.; Sutherland, T. C.; Nyulászi, L.; Baumgartner, T. *Chem. Eur. J.* 14, 9878 (2008), which is incorporated herein by reference.

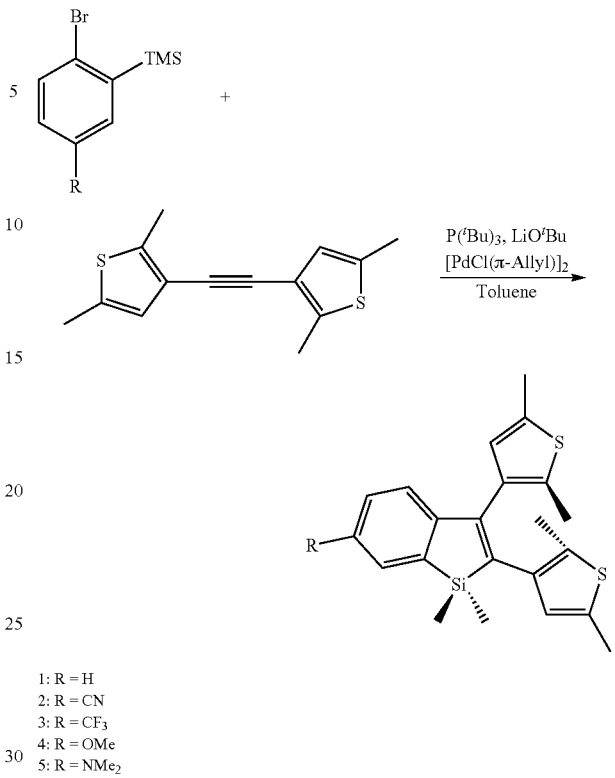

1: R = H
2: R = CN
3: R = CF$_3$
4: R = OMe
5: R = NMe$_2$

Scheme 1 Synthetic pathway for compounds 1-5

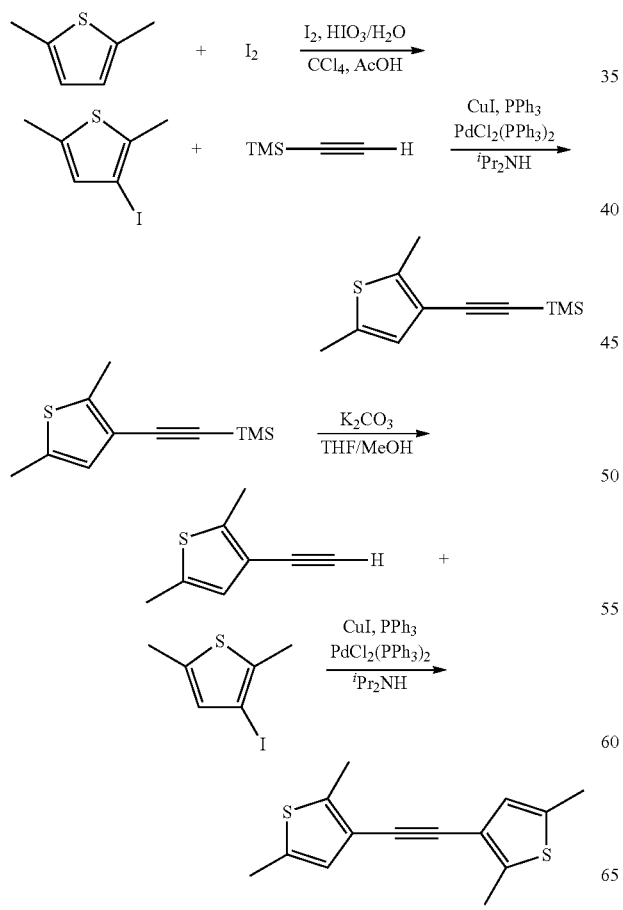

Scheme 2 Synthetic pathway for compounds 6-8

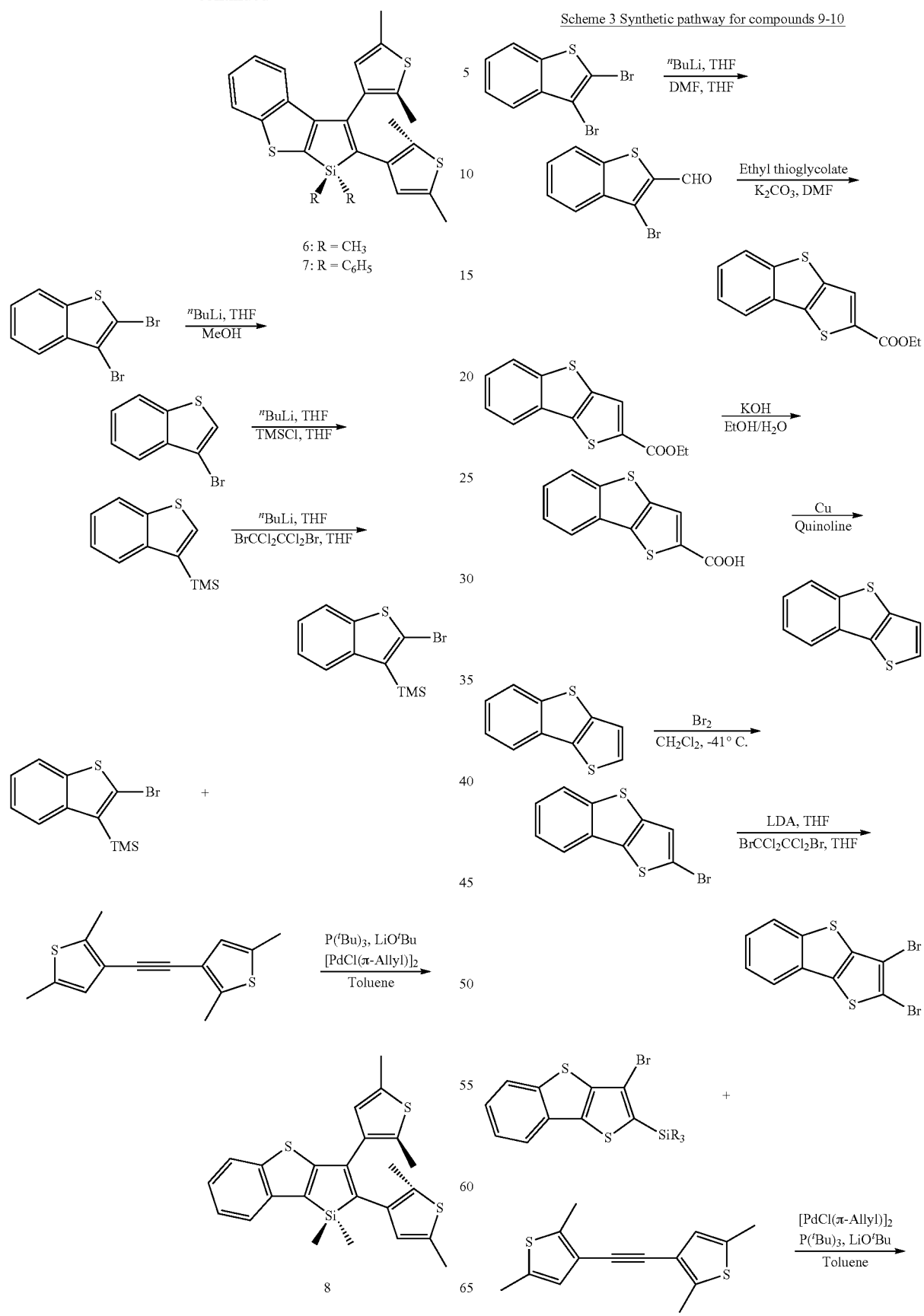

-continued
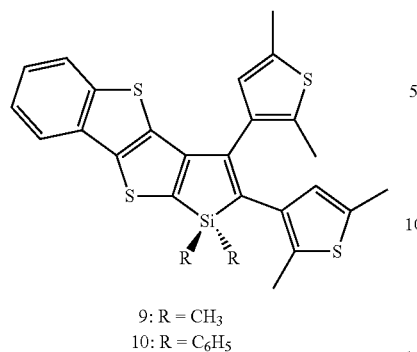
9: R = CH₃
10: R = C₆H₅
Scheme 4 Synthetic pathway for compound 11
Scheme 5 Synthetic pathway for compounds 12-16
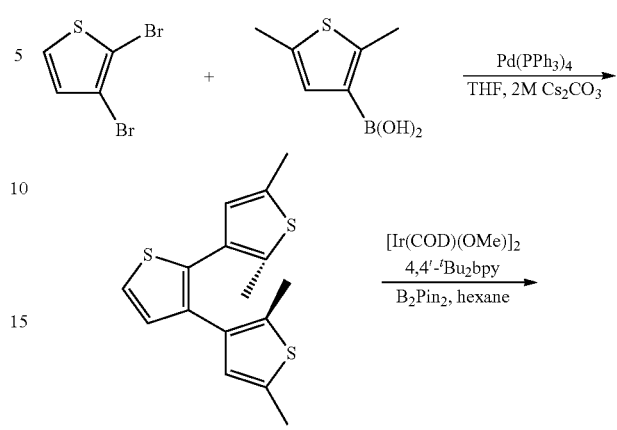
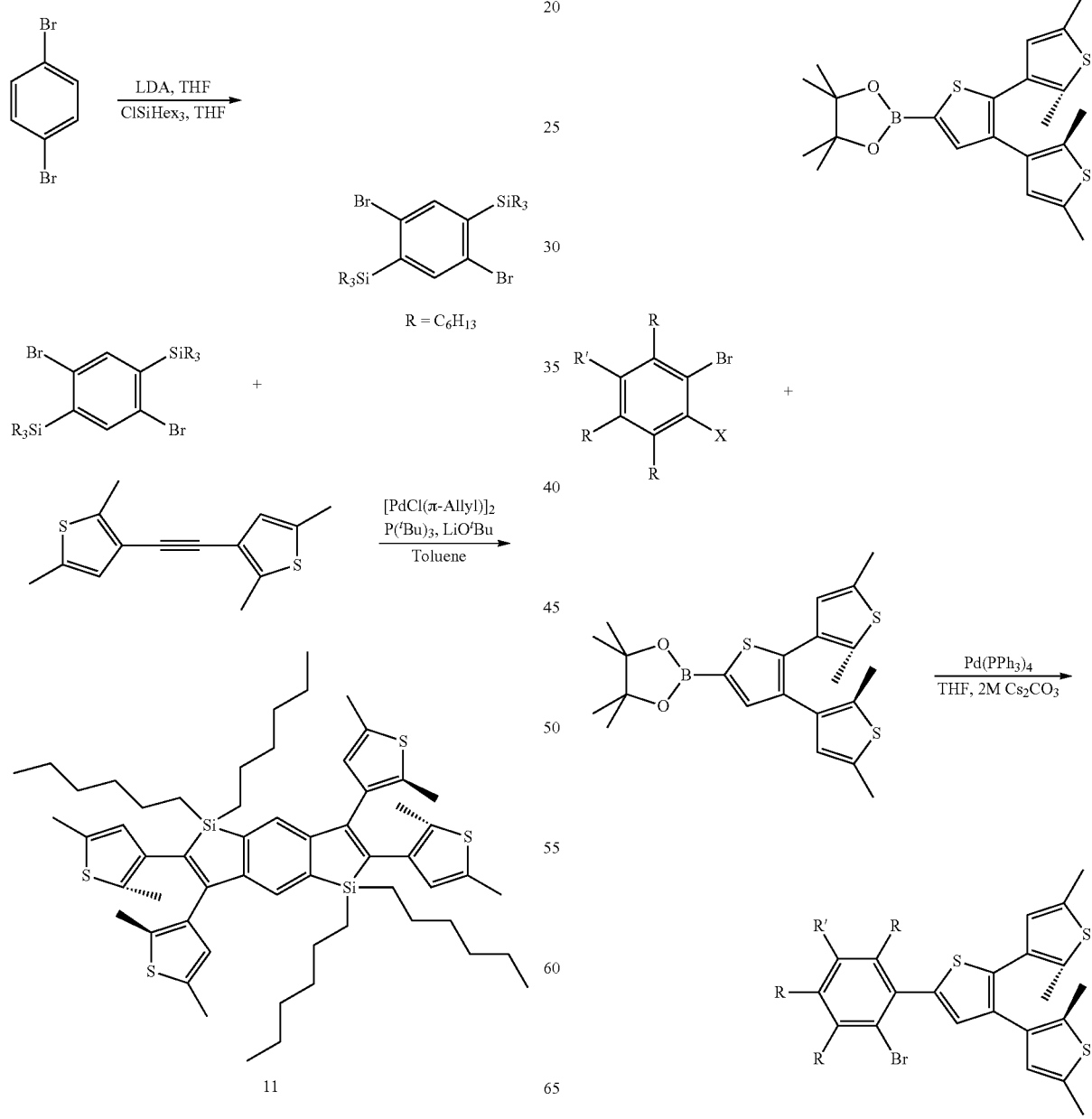

21
-continued
22
-continued
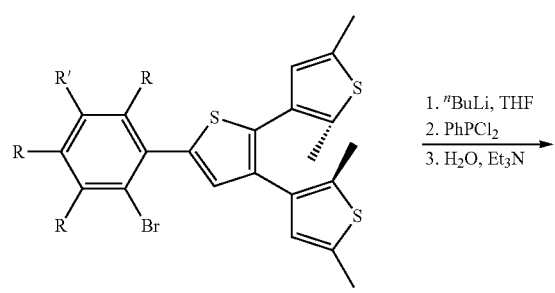
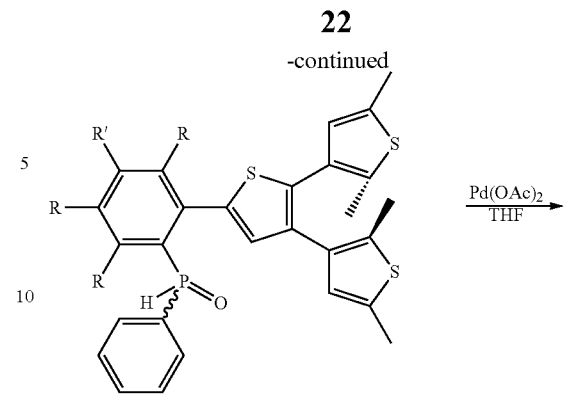
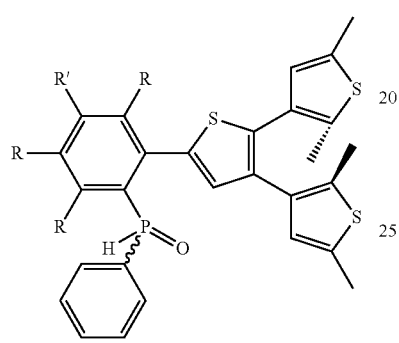
12 X = Br, R = R' = H
13 X = Br, R = R' = F
14 X = I, R = H, R' = CF₃
15 X = I, R = H, R' = CH₃
16 X = I, R = H, R' = OCH₃
Scheme 6 Synthetic pathway for compounds 17-20
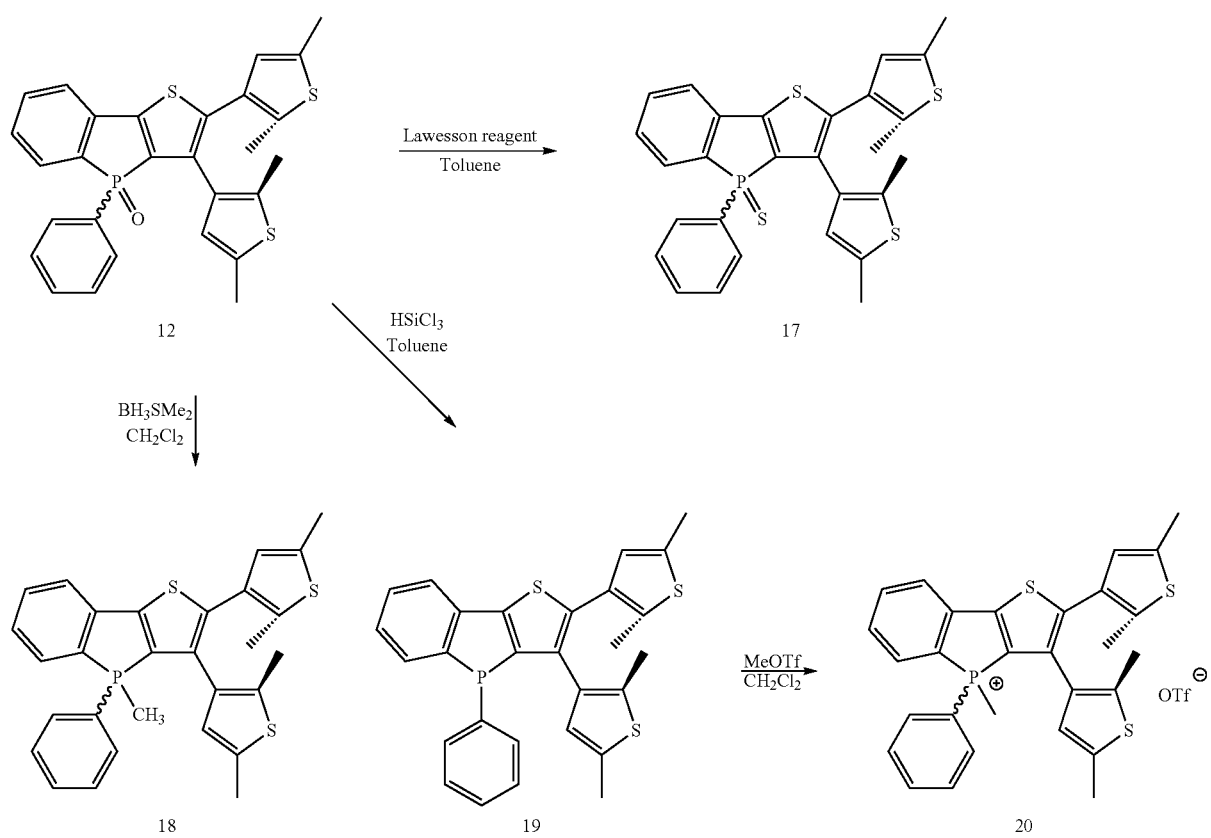

Scheme 7 Synthetic pathway for compounds 21-22
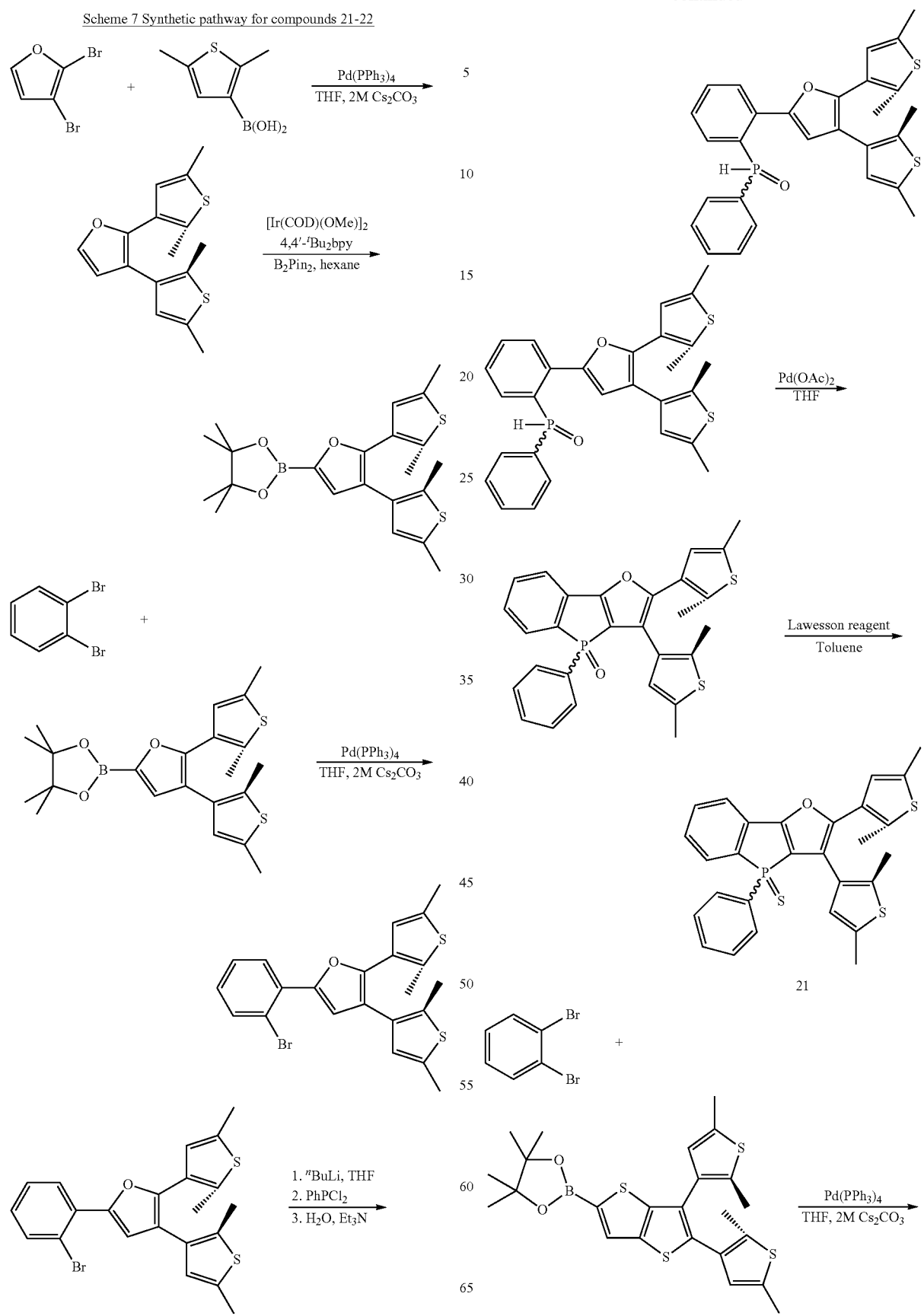

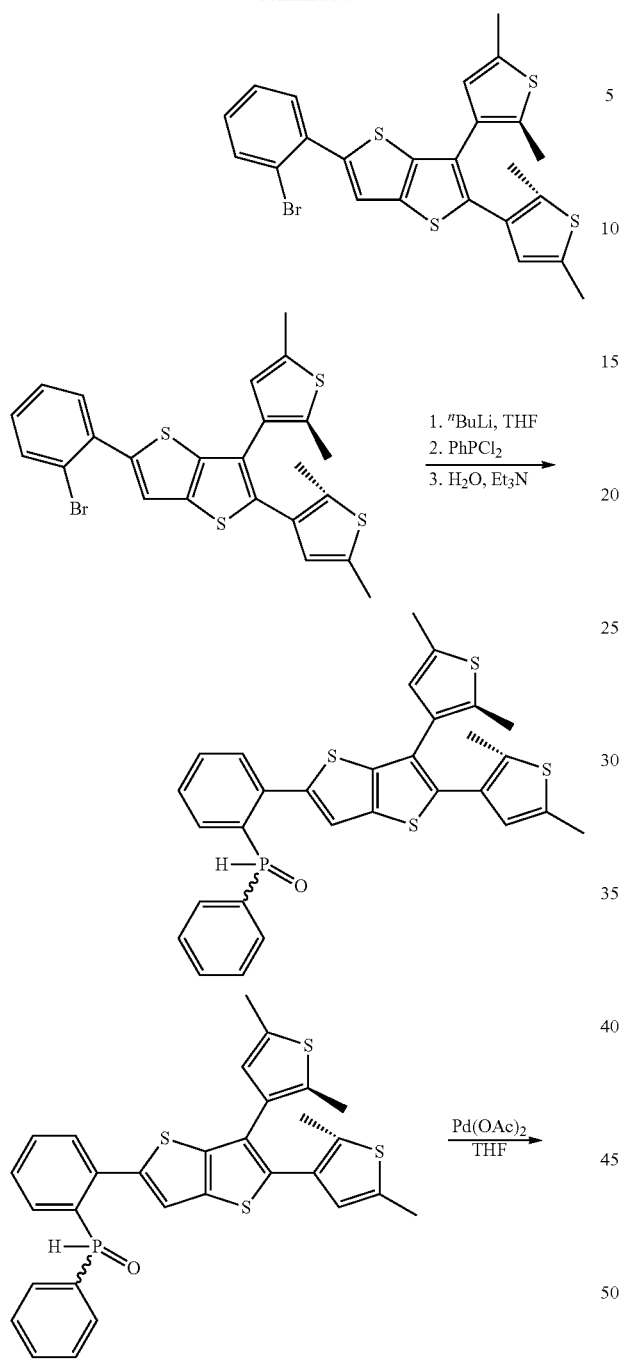
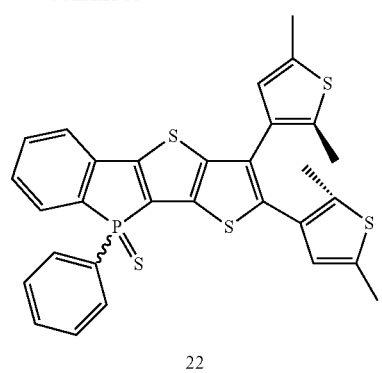
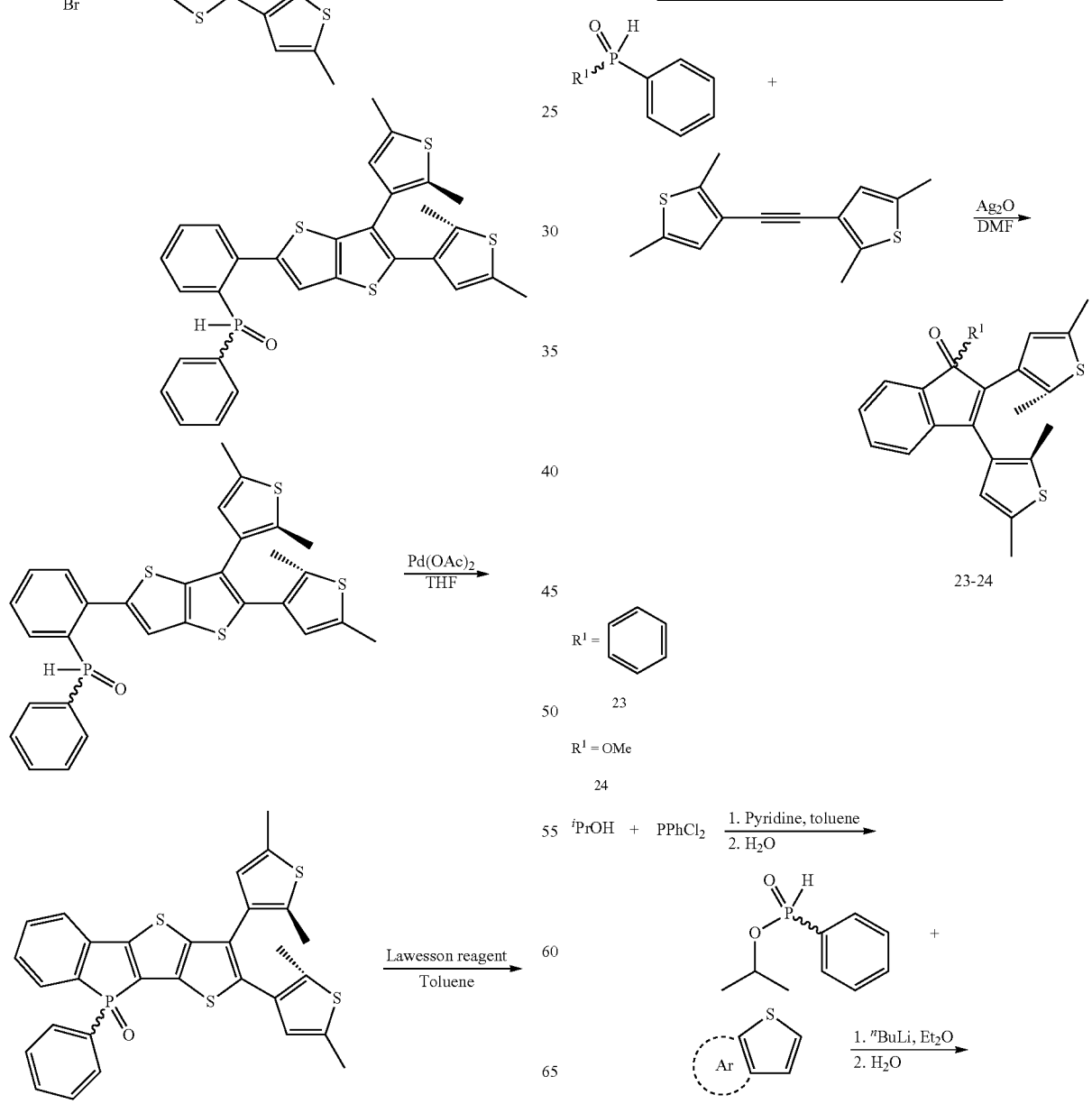
Scheme 8 Synthetic pathway for compounds 23-28

27
-continued
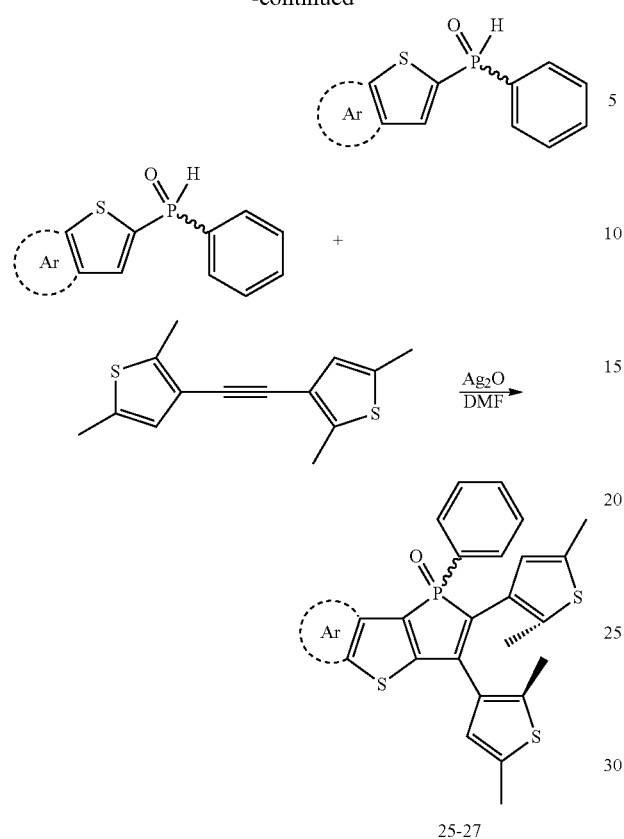
28
-continued
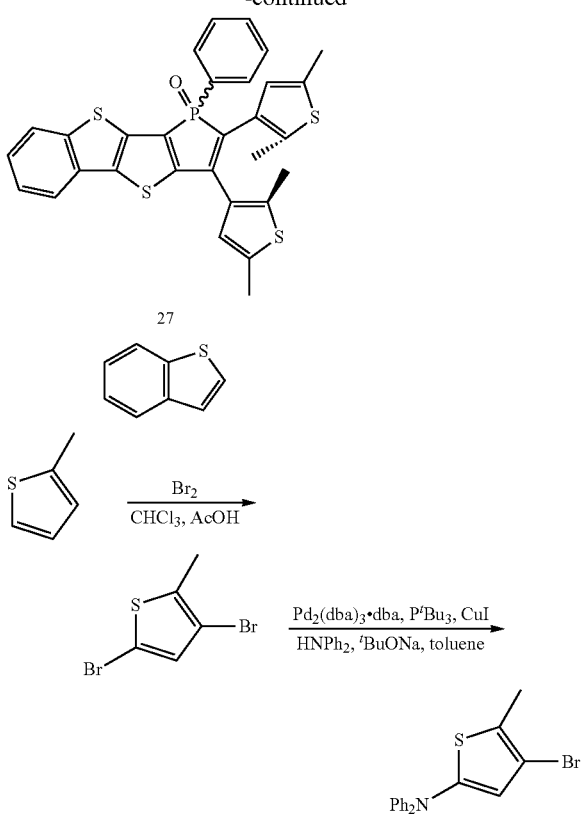

29
-continued
30
-continued
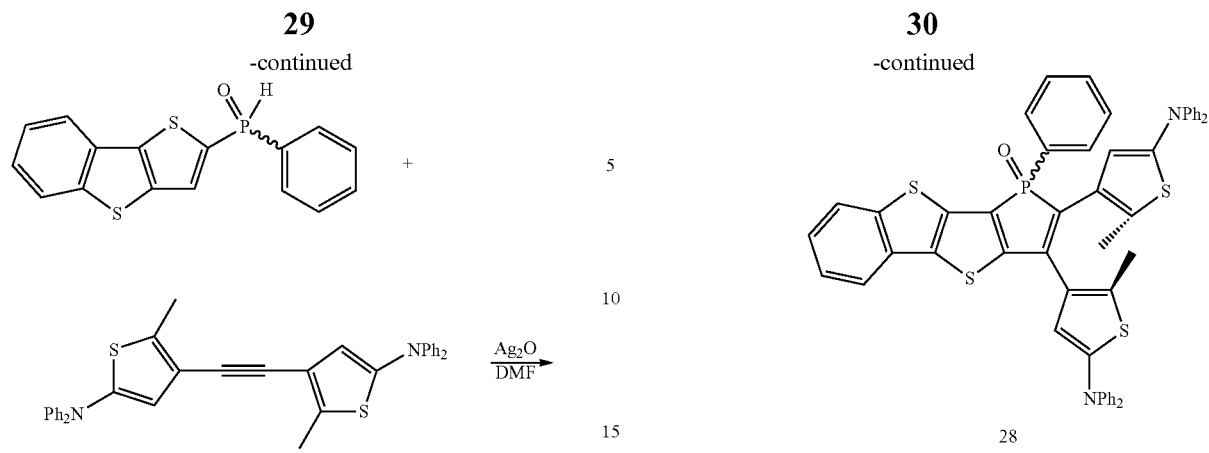
Scheme 9 Synthetic pathway for compounds 29-32
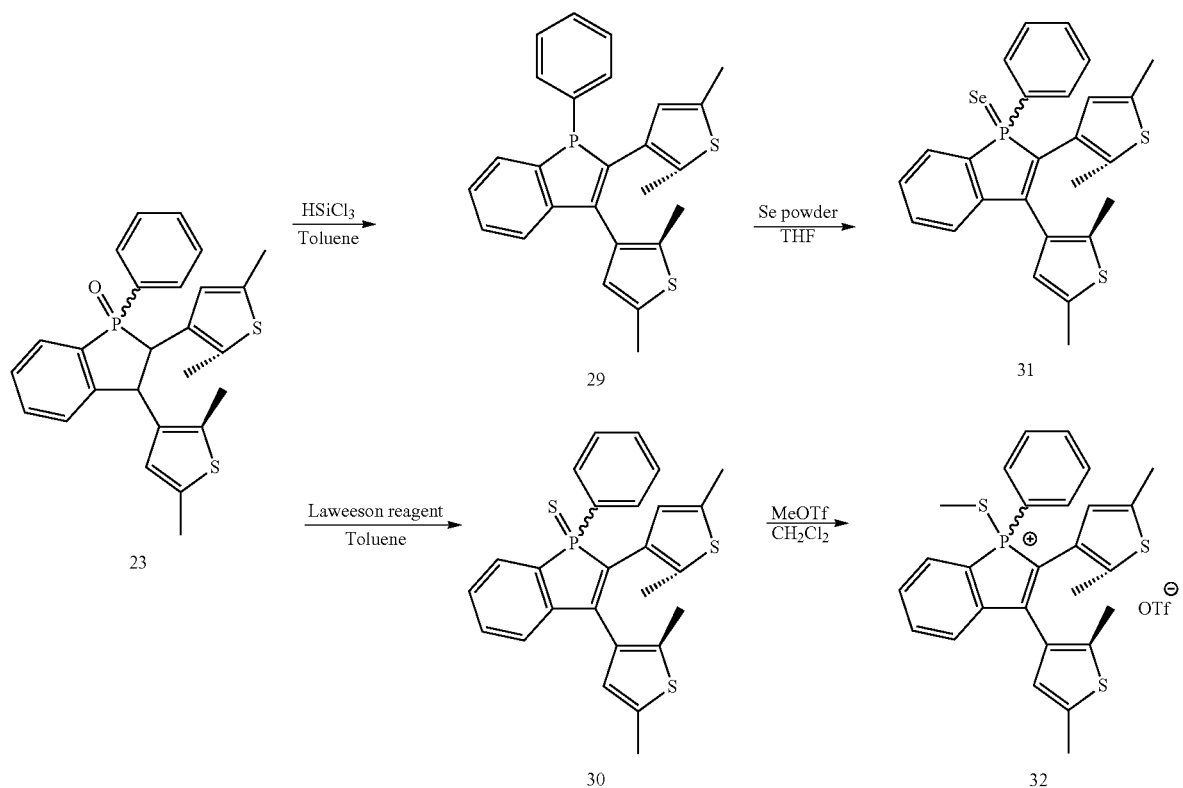
Scheme 10 Synthetic pathway for compound 33
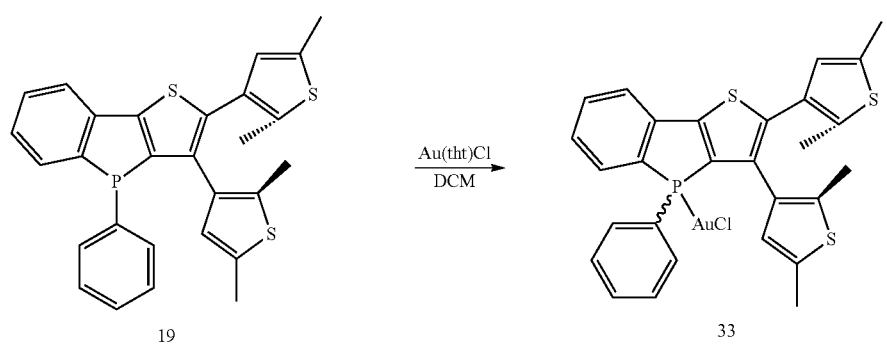

Generally, the compounds show improvement in the photocyclization and photocycloreversion, and have improved photochromic behavior. The characteristic spectroscopic properties of compounds 1-33 are as follows:

Compound 1 [BzSiMe$_2$-DTE] Yield: 55%. $^1$H NMR (300 MHz, CDCl$_3$, 298 K): δ 0.31 (s, 3H, Si—CH$_3$), 0.46 (s, 3H, Si—CH$_3$), 1.87 (s, 3H, —CH$_3$), 1.94 (s, 3H, —CH$_3$), 2.37 (s, 3H, —CH$_3$), 2.40 (s, 3H, —CH$_3$), 6.32 (s, 1H, thienyl), 6.46 (s, 1H, thienyl), 7.16 (d, J=7.4 Hz, 1H, phenyl), 7.15-7.18 (m, 1H, phenyl), 7.31 (td, J=7.4, 1.4 Hz, 1H, phenyl), 7.57-7.60 (m, 1H, phenyl). Positive EI-MS, m/z: 380. HRMS (Positive EI) calcd for C$_{22}$H$_{24}$$^{32}$S$_2$$^{28}$Si: m/z=380.1083. found: 380.1083 [M]$^+$. Elemental analyses. Found (%): C, 67.38; H, 6.97; Calcd (%) for C$_{22}$H$_{24}$S$_2$Si—CH$_3$CH$_2$OH: C, 67.55; H, 7.09.

Compound 2 [NCBzSiMe$_2$-DTE] Yield: 57%. $^1$H NMR (400 MHz, CDCl$_3$, 298 K): δ 0.33 (s, 3H, Si—CH$_3$), 0.48 (s, 3H, Si—CH$_3$), 1.86 (s, 3H, —CH$_3$), 1.91 (s, 3H, —CH$_3$), 2.36 (s, 3H, —CH$_3$), 2.40 (s, 3H, —CH$_3$), 6.30 (s, 1H, thienyl), 6.40 (s, 1H, thienyl), 7.21 (d, J=8.0 Hz, 1H, phenyl), 7.58 (dd, J=8.0, 1.7 Hz, 1H, phenyl), 7.79 (d, J=1.7 Hz, 1H, phenyl). Positive EI-MS, m/z: 405. HRMS (Positive EI) calcd for C$_{23}$H$_{23}$N$^{32}$S$_2$$^{28}$Si: m/z=405.1036. found: 405.1037 [M]$^+$. Elemental analyses. Found (%): C, 68.01; H, 5.75; N, 3.57; Calcd (%) for C$_{23}$H$_{23}$NS$_2$Si: C, 68.10; H, 5.71; N, 3.45.

Compound 3 [CF$_3$BzSiMe$_2$-DTE] Yield: 53%. $^1$H NMR (400 MHz, CDCl$_3$, 298 K): δ 0.34 (s, 3H, Si—CH$_3$), 0.48 (s, 3H, Si—CH$_3$), 1.87 (s, 3H, —CH$_3$), 1.93 (s, 3H, —CH$_3$), 2.36 (s, 3H, —CH$_3$), 2.40 (s, 3H, —CH$_3$), 6.31 (s, 1H, thienyl), 6.42 (s, 1H, thienyl), 7.23 (d, J=8.1 Hz, 1H, phenyl), 7.54 (d, J=8.1 Hz, 1H, phenyl), 7.78 (s, 1H, phenyl). $^{19}$F NMR (376.4 MHz, CDCl$_3$, 298 K): δ −61.99. Positive EI-MS, m/z: 448. HRMS (Positive EI) calcd for C$_{23}$H$_{23}$F$_3$$^{32}$S$_2$$^{28}$Si: m/z=448.0957. found: 448.0964 [M]$^+$. Elemental analyses. Found (%): C, 61.65; H, 5.26; Calcd (%) for C$_{23}$H$_{23}$F$_3$S$_2$Si: C, 61.57; H, 5.17.

Compound 4 [MeOBzSiMe$_2$-DTE] Yield: 64%. $^1$H NMR (300 MHz, CDCl$_3$, 298 K): δ 0.31 (s, 3H, Si—CH$_3$), 0.46 (s, 3H, Si—CH$_3$), 1.88 (s, 3H, —CH$_3$), 1.95 (s, 3H, —CH$_3$), 2.37 (s, 3H, —CH$_3$), 2.40 (s, 3H, —CH$_3$), 3.85 (s, 3H, —OCH$_3$), 6.32 (s, 1H, thienyl), 6.46 (s, 1H, thienyl), 6.81 (dd, J=8.4, 2.6 Hz, 1H, phenyl), 7.09 (d, J=8.4 Hz, 1H, phenyl), 7.16 (d, J=2.6 Hz, 1H, phenyl). Positive EI-MS, m/z: 410. HRMS (Positive EI) calcd for C$_{23}$H$_{26}$O$^{32}$S$_2$$^{28}$Si: m/z=410.1189. found: 410.1189 [M]$^+$. Elemental analyses. Found (%): C, 66.96; H, 6.39; Calcd (%) for C$_{23}$H$_{26}$OS$_2$Si: C, 67.27; H, 6.38.

Compound 5 [Me$_2$NBzSiMe$_2$-DTE] Yield: 58%. $^1$H NMR (500 MHz, CDCl$_3$, 298 K): δ 0.30 (s, 3H, Si—CH$_3$), 0.45 (s, 3H, Si—CH$_3$), 1.87 (s, 3H, —CH$_3$), 1.93 (s, 3H, —CH$_3$), 2.35 (s, 3H, —CH$_3$), 2.39 (s, 3H, —CH$_3$), 2.99 (s, 6H, —N(CH$_3$)$_2$), 6.30 (s, 1H, thienyl), 6.46 (s, 1H, thienyl), 6.64 (dd, J=8.5, 2.5 Hz, 1H, phenyl), 7.03-7.16 (m, 2H, phenyl). Positive EI-MS, m/z: 423. HRMS (Positive EI) calcd for C$_{24}$H$_{29}$N$^{32}$S$_2$$^{28}$Si: m/z=423.1505. found: 423.1511 [M]$^+$. Elemental analyses. Found (%): C, 67.47; H, 6.97; N, 3.30; Calcd (%) for C$_{24}$H$_{29}$NS$_2$Si.0.5(CH$_3$CH$_2$OH): C, 67.21; H, 7.22; N, 3.14.

Compound 6 [cis-BzThSiMe$_2$-DTE] Yield: 68%. $^1$H NMR (400 MHz, CDCl$_3$, 298 K): δ 0.41 (s, 3H, Si—CH$_3$), 0.49 (s, 3H, Si—CH$_3$), 2.02 (s, 6H, —CH$_3$), 2.35 (s, 3H, —CH$_3$), 2.41 (s, 3H, —CH$_3$), 6.26 (s, 1H, thienyl), 6.46 (s, 1H, thienyl), 7.10-7.17 (m, 2H, phenyl), 7.22-7.26 (m, 1H, phenyl), 7.87 (d, J=8.1 Hz, 1H, phenyl). Positive EI-MS, m/z: 436. HRMS (Positive EI) calcd for C$_{24}$H$_{24}$$^{32}$S$_3$$^{28}$Si: m/z=436.0804. found: 436.0805 [M]$^+$. Elemental analyses. Found (%): C, 66.01; H, 5.55; Calcd (%) for C$_{24}$H$_{24}$S$_3$Si: C, 66.00; H, 5.54.

Compound 7 [cis-BzThSiPh$_2$-DTE] Yield: 49%. $^1$H NMR (400 MHz, CDCl$_3$, 298 K): δ 1.75 (s, 3H, —CH$_3$), 2.03 (s, 3H, —CH$_3$), 2.24 (s, 3H, —CH$_3$), 2.40 (s, 3H, —CH$_3$), 6.08 (s, 1H, thienyl), 6.49 (s, 1H, thienyl), 7.18-7.20 (m, 2H, phenyl), 7.24-7.28 (m, 1H, phenyl), 7.33-7.36 (m, 4H, phenyl), 7.39-7.45 (m, 2H, phenyl), 7.55-7.59 (m, 4H, phenyl) 7.88 (d, J=8.1 Hz, 1H, phenyl). Positive EI-MS, m/z: 560. HRMS (Positive EI) calcd for C$_{34}$H$_{28}$$^{32}$S$_3$$^{28}$Si: m/z=560.1123. found: 560.1120 [M]$^+$. Elemental analyses. Found (%): C, 71.93; H, 5.06; Calcd (%) for C$_{34}$H$_{28}$S$_3$Si.0.5 (CH$_3$CH$_2$OH): C, 72.00; H, 5.35.

Compound 8 [trans-BzThSiMe$_2$-DTE] Yield: 71%. $^1$H NMR (300 MHz, CDCl$_3$, 298 K): δ 0.38 (s, 3H, Si—CH$_3$), 0.58 (s, 3H, Si—CH$_3$), 1.84 (s, 3H, —CH$_3$), 1.93 (s, 3H, —CH$_3$), 2.38 (s, 3H, —CH$_3$), 2.43 (s, 3H, —CH$_3$), 6.39 (s, 1H, thienyl), 6.72 (s, 1H, thienyl), 7.21-7.28 (m, 1H, phenyl), 7.32-7.37 (m, 1H, phenyl), 7.72 (d, J=7.7 Hz, 1H, phenyl), 7.82 (d, J=8.0 Hz, 1H, phenyl). Positive EI-MS, m/z: 436. HRMS (Positive EI) calcd for C$_{24}$H$_{24}$$^{32}$S$_3$$^{28}$Si: m/z=436.0804. found: 436.0806 [M]$^+$. Elemental analyses. Found (%): C, 65.5; H, 5.65; Calcd (%) for C$_{24}$H$_{24}$S$_3$Si.0.5 (CH$_3$CH$_2$OH): C, 65.31; H, 5.92.

Compound 9 [cis-BzTThSiMe$_2$-DTE] Yield: 47%. $^1$H NMR (300 MHz, CDCl$_3$, 298 K): δ 0.44 (s, 3H, Si—CH$_3$), 0.52 (s, 3H, Si—CH$_3$), 1.95 (s, 3H, —CH$_3$), 2.05 (s, 3H, —CH$_3$), 2.37 (s, 3H, —CH$_3$), 2.45 (s, 3H, —CH$_3$), 6.33 (s, 1H, thienyl), 6.50 (s, 1H, thienyl), 7.26-7.39 (m, 2H, phenyl), 7.73 (d, J=8.1 Hz, 1H, phenyl), 7.94 (d, J=8.5 Hz, 1H, phenyl). Positive EI-MS, m/z: 492. HRMS (Positive EI) calcd for C$_{26}$H$_{24}$$^{32}$S$_4$$^{28}$Si: m/z=492.0525. found: 492.0520 [M]$^+$. Elemental analyses. Found (%): C, 63.40; H, 4.94; Calcd (%) for C$_{26}$H$_{24}$S$_4$Si: C, 63.37; H, 4.91.

Compound 10 [cis-BzTThSiPh$_2$-DTE] Yield: 60%. $^1$H NMR (300 MHz, CDCl$_3$, 298 K): δ 1.78 (s, 3H, —CH$_3$), 2.06 (s, 3H, —CH$_3$), 2.25 (s, 3H, —CH$_3$), 2.47 (s, 3H, —CH$_3$), 6.11 (s, 1H, thienyl), 6.57 (s, 1H, thienyl), 7.29-7.33 (m, 1H, phenyl), 7.36-7.39 (m, 5H, phenyl), 7.43-7.47 (m, 2H, phenyl), 7.59-7.60 (m, 2H, phenyl), 7.75 (d, J=7.9 Hz, 1H, phenyl), 7.85 (d, J=8.0 Hz, 1H, phenyl). Positive EI-MS, m/z: 617. HRMS (Positive EI) calcd for C$_{36}$H$_{28}$$^{32}$S$_4$$^{28}$Si: m/z=616.0839. found: 616.0840 [M]$^+$. Elemental analyses. Found (%): C, 69.81; H, 4.59; Calcd (%) for C$_{36}$H$_{28}$S$_4$Si: C, 70.08; H, 4.57.

Compound 11 [DTE-SiHex$_2$BzSiHex$_2$-DTE] Yield: 51%. $^1$H NMR (500 MHz, CDCl$_3$, 298 K): δ 0.79-0.97 (m, 20H, hexyl), 1.14-1.26 (m, 32H, hexyl), 1.80 (s, 6H, —CH$_3$), 1.96 (s, 3H, —CH$_3$), 1.98 (s, 3H, —CH$_3$), 2.37 (s, 6H, —CH$_3$), 2.40 (s, 6H, —CH$_3$), 6.31 (s, 2H, thienyl), 6.41 (s, 1H, thienyl), 6.44 (s, 1H, thienyl), 7.33 (s, 1H, phenyl), 7.34 (s, 1H, phenyl). Positive EI-MS, 717/Z: 963. HRMS (Positive EI) calcd for C$_{58}$H$_{82}$$^{32}$S$_4$$^{28}$Si$_2$: m/z=962.4832. found: 962.4790 [M]$^+$. Elemental analyses. Found (%): C, 72.04; H, 8.63; Calcd (%) for C$_{58}$H$_{82}$S$_4$Si$_2$: C, 72.29; H, 8.58.

Compound 12 [C$_6$H$_4$PhP(O)Th-DTE] Yield: 36%. $^1$H NMR (400 MHz, [D$_6$]DMSO, 353 K): δ 1.73 (s, 3H, —CH$_3$), 2.09 (s, 3H, —CH$_3$), 2.28 (s, 3H, —CH$_3$), 2.32 (s, 3H, —CH$_3$), 6.38 (s, 1H, thienyl), 6.52 (s, 1H, thienyl), 7.38-7.45 (m, 5H, phenyl), 7.50-7.54 (m, 1H, phenyl), 7.60-7.68 (m, 3H, phenyl). $^{31}$P{$^1$H} NMR (162 MHz, CDCl$_3$, 298 K): δ 26.0. Positive EI-MS, m/z: 502. HRMS (Positive EI) calcd for C$_{28}$H$_{23}$OP$^{32}$S$_3$: m/z=502.0643. found: 502.0646 [M]$^+$. Elemental analyses. Found (%): C, 65.36; H, 4.83; Calcd (%) for C$_{28}$H$_{23}$OPS$_3$.CH$_3$OH: C, 65.14; H, 5.09.

Compound 13 [C$_6$F$_4$PhP(O)Th-DTE] Yield: 23%. $^1$H NMR (400 MHz, [D$_6$]DMSO, 353 K): δ 1.64 (s, 3H, —CH$_3$), 2.05 (s, 3H, —CH$_3$), 2.21 (s, 3H, —CH$_3$), 2.26 (s, 3H, —CH$_3$), 6.30 (s, 1H, thienyl), 6.47 (s, 1H, thienyl), 7.40-7.47 (m, 4H, phenyl), 7.56-7.60 (m, 1H, phenyl). $^{19}$F NMR (376.4 MHz, CDCl$_3$, 298 K): δ −133.1-(−133.2) (m, 1F, C$_6$F$_4$), −141.4-(−141.5) (m, 1F, C$_6$F$_4$), −146.0-(−146.1) (m, 1F, C$_6$F$_4$), −153.2 (t, J=20.7 Hz, 1F, C$_6$F$_4$) $^{31}$P{$^1$H} NMR (162 MHz, CDCl$_3$, 298 K): δ 24.5. Positive EI-MS, m/z: 574. HRMS (Positive EI) calcd for C$_{28}$H$_{19}$OF$_4$P$^{32}$S$_3$: m/z=574.0266. found: 574.0260 [M]$^+$. Elemental analyses. Found (%): C, 58.01; H, 3.39; Calcd (%) for C$_{28}$H$_{19}$OF$_4$PS$_3$.0.5(CH$_3$OH): C, 57.96; H, 3.58.

Compound 14 [CF$_3$C$_6$H$_3$PhP(O)Th-DTE] Yield: 28%. $^1$H NMR (400 MHz, [D$_6$]DMSO, 353 K): δ 1.74 (s, 3H, —CH$_3$), 2.12 (s, 3H, —CH$_3$), 2.27 (s, 3H, —CH$_3$), 2.33 (s, 3H, —CH$_3$), 6.36 (s, 1H, thienyl), 6.54 (s, 1H, thienyl), 7.38-7.48 (m, 4H, phenyl), 7.53-7.58 (m, 1H, phenyl), 7.88-7.98 (m, 3H, phenyl). $^{19}$F NMR (376.4 MHz, CDCl$_3$, 298 K): δ −60.9. $^{31}$P{$^1$H} NMR (162 MHz, CDCl$_3$, 298 K): δ 23.0. Positive EI-MS, m/z: 570. HRMS (Positive EI) calcd for C$_{29}$H$_{22}$OF$_3$P$^{32}$S$_3$: m/z=570.0517. found: 570.0516 [M]$^+$. Elemental analyses. Found (%): C, 60.37; H, 3.95; Calcd (%) for C$_{29}$H$_{22}$OF$_3$PS$_3$.0.5(CH$_3$OH): C, 60.39; H, 4.12.

Compound 15 [CH$_3$C$_6$H$_3$PhP(O)Th-DTE] Yield: 29%. $^1$H NMR (400 MHz, [D$_6$]DMSO, 353 K): δ 1.73 (s, 3H, —CH$_3$), 2.10 (s, 3H, —CH$_3$), 2.27 (s, 3H, —CH$_3$), 2.32 (s, 3H, —CH$_3$), 2.37 (s, 3H, —CH$_3$), 6.36 (s, 1H, thienyl), 6.51 (s, 1H, thienyl), 7.48-7.35 (m, 6H, phenyl), 7.58-7.48 (m, 2H, phenyl). $^{31}$P{$^1$H} NMR (162 MHz, CDCl$_3$, 298 K): δ 25.8. Positive EI-MS, m/z: 516. HRMS (Positive EI) calcd for C$_{29}$H$_{25}$OP$^{32}$S$_3$: m/z=516.0800. found: 516.0798 [M]$^+$. Elemental analyses. Found (%): C, 65.80; H, 5.25; Calcd (%) for C$_{29}$H$_{25}$OPS$_3$—CH$_3$OH: C, 65.67; H, 5.33.

Compound 16 [MeOC$_6$H$_3$PhP(O)Th-DTE] Yield: 47%. NMR (400 MHz, [D$_6$]DMSO, 353 K): δ 1.73 (s, 3H, —CH$_3$), 2.09 (s, 3H, —CH$_3$), 2.27 (s, 3H, —CH$_3$), 2.31 (s, 3H, —CH$_3$), 3.83 (s, 3H, —CH$_3$), 6.36 (s, 1H, thienyl), 6.50 (s, 1H, thienyl), 7.14-7.21 (m, 2H, phenyl), 7.35-7.43 (m, 4H, phenyl), 7.48-7.54 (m, 1H, phenyl), 7.57-7.60 (m, 1H, phenyl). $^{31}$P{$^1$H} NMR (162 MHz, CDCl$_3$, 298 K): δ 23.8. Positive EI-MS, m/z: 532. HRMS (Positive EI) calcd for C$_{29}$H$_{25}$O$_2$P$^{32}$S$_3$: m/z=532.0749. found: 532.0743 [M]$^+$. Elemental analyses. Found (%): C, 65.15; H, 5.02; Calcd (%) for C$_{29}$H$_{25}$O$_2$PS$_3$: C, 65.39; H, 4.73.

Compound 17 [C$_6$H$_4$PhP(S)Th-DTE] Yield: 72%. NMR (400 MHz, [D$_6$]DMSO, 353 K): δ 1.64 (s, 3H, —CH$_3$), 2.13 (s, 3H, —CH$_3$), 2.26 (s, 3H, —CH$_3$), 2.30 (s, 3H, —CH$_3$), 6.34 (s, 1H, thienyl), 6.49 (s, 1H, thienyl), 7.39-7.66 (m, 8H, phenyl), 7.72-7.75 (m, 1H, phenyl). $^{31}$P{$^1$H} NMR (162 MHz, CDCl$_3$, 298 K): δ 33.4. Positive EI-MS, m/z: 518. HRMS (Positive EI) calcd for C$_{28}$H$_{23}$P$^{32}$S$_4$: m/z=518.0415. found: 518.0414 [M]$^+$. Elemental analyses. Found (%): C, 64.92; H, 4.47; Calcd (%) for C$_{28}$H$_{23}$PS$_4$: C, 64.83; H, 4.47.

Compound 18 [C$_6$H$_4$PhP(BH$_3$)Th-DTE] Yield: 62%. $^1$H NMR (400 MHz, CDCl$_3$, 298 K): δ 1.61 (s, 3H, —BH$_3$), 1.73 (s, 3H, —CH$_3$), 2.11 (s, 3H, —CH$_3$), 2.30 (s, 3H, —CH$_3$), 2.34 (s, 3H, —CH$_3$), 6.25 (s, 1H, thienyl), 6.45 (s, 1H, thienyl), 7.13-7.25 (m, 6H, phenyl), 7.39-7.43 (m, 1H, phenyl), 7.60-7.64 (m, 2H, phenyl). $^{11}$B{$^1$H} NMR (160.5 MHz, CDCl$_3$, 298 K, relative to BF$_3$.OEt$_2$): δ −36.1. $^{31}$P{$^1$H} NMR (162 MHz, CDCl$_3$, 298 K): δ 21.6. Positive EI-MS, m/z: 486. HRMS (Positive EI) calcd for C$_{28}$H$_{23}$P$^{32}$S$_3$: m/z=486.0694. found: 486.0675 [M-BH$_3$]$^+$. Elemental analyses. Found (%): C, 66.01; H, 5.55; Calcd (%) for C$_{28}$H$_{26}$BPS$_3$.0.5(H$_2$O): C, 66.01; H, 5.34.

Compound 19 [C$_6$H$_4$PhPTh-DTE] Yield: 83%. $^1$H NMR (400 MHz, CDCl$_3$, 298 K): δ 1.74 (s, 3H, —CH$_3$), 2.12 (s, 3H, —CH$_3$), 2.31 (s, 3H, —CH$_3$), 2.35 (s, 3H, —CH$_3$), 6.25 (s, 1H, thienyl), 6.46 (s, 1H, thienyl), 7.14-7.25 (m, 6H, phenyl), 7.41 (td, J=7.5, 1.1 Hz, 1H, phenyl), 7.61-7.65 (m, 2H, phenyl). $^{31}$P{$^1$H} NMR (162 MHz, CDCl$_3$, 298 K): δ −15.6. Positive EI-MS, m/z: 486. HRMS (Positive EI) calcd for C$_{28}$H$_{23}$P$^{32}$S$_3$: m/z=486.0694. found: 486.0685 [M]$^+$. Elemental analyses. Found (%): C, 66.79; H, 4.77; Calcd (%) for C$_{28}$H$_{23}$PS$_3$.(H$_2$O): C, 66.64; H, 4.99.

Compound 20 {[C$_6$H$_4$PhP(CH$_3$)Th-DTE](OTf)} Yield: 73%. $^1$H NMR (400 MHz, [D$_6$]DMSO, 373 K): δ 1.64 (s, 3H, —CH$_3$), 2.17 (s, 3H, —CH$_3$), 2.27 (s, 6H, —CH$_3$), 2.63 (d, 3H, P—CH$_3$), 6.28 (s, 1H, thienyl), 6.47 (s, 1H, thienyl), 7.46-7.60 (m, 5H, phenyl), 7.74-7.80 (m, 1H, phenyl), 7.86 (t, J=7.4 Hz 1H, phenyl), 7.92-7.96 (m, 1H, phenyl), 8.05-8.12 (m, 1H, phenyl). $^{31}$P{$^1$H} NMR (162 MHz, CDCl$_3$, 298 K): δ 18.2. Positive EI-MS, m/z: 501. HRMS (Positive EI) calcd for C$_{29}$H$_{26}$P$^{32}$S$_3$: m/z=501.0929. found: 501.0923 {M}. Elemental analyses. Found (%): C, 54.64; H, 4.08; Calcd (%) for C$_{29}$H$_{26}$PS$_3$(CF$_3$SO$_3$).0.5(H$_2$O): C, 54.61; H, 4.12.

Compound 21 [C$_6$H$_4$PhP(S)Furan-DTE] Yield: 85%. $^1$H NMR (400 MHz, CDCl$_3$, 298 K): δ 1.84 (s, 3H, —CH$_3$), 2.21 (s, 3H, —CH$_3$), 2.34 (s, 3H, —CH$_3$), 2.38 (s, 3H, —CH$_3$), 6.60 (s, 2H, thienyl), 7.32-7.38 (m, 3H, phenyl), 7.43-7.51 (m, 2H, phenyl), 7.53-7.59 (m, 1H, phenyl), 7.66 (dd, J=11.8, 7.4 Hz, 1H, phenyl), 7.70-7.78 (m, 2H, phenyl). $^{31}$P{$^1$H} NMR (162 MHz, CDCl$_3$, 298 K): δ 27.81. Positive EI-MS, m/z: 502. HRMS (Positive EI) calcd for C$_{28}$H$_{23}$OP$^{32}$S$_3$: m/z=502.0643. found: 502.0643 [M]. Elemental analyses. Found (%): C, 67.00; H, 4.77; Calcd (%) for C$_{28}$H$_{23}$OPS$_3$: C, 66.90; H, 4.61.

Compound 22 [C$_6$H$_4$PhP(S)TTh-DTE] Yield: 75%. $^1$H NMR (400 MHz, CDCl$_3$, 298 K): δ 1.97 (s, 3H, —CH$_3$), 2.02 (s, 3H, —CH$_3$), 2.35 (s, 3H, —CH$_3$), 2.45 (s, 3H, —CH$_3$), 6.48 (s, 1H, thienyl), 6.65 (s, 1H, thienyl), 7.31-7.38 (m, 1H, phenyl), 7.38-7.55 (m, 5H, phenyl), 7.67 (dd, J=11.4, 7.4 Hz, 1H, phenyl), 7.86 (dd, J=14.8, 7.2 Hz, 1H, phenyl). $^{31}$P{$^1$H} NMR (162 MHz, CDCl$_3$, 298 K): δ 32.27. Positive EI-MS, m/z: 574. HRMS (Positive EI) calcd for C$_{30}$H$_{23}$P$^{32}$S$_5$: m/z=574.0135. found: 574.0132 [M]$^+$. Elemental analyses. Found (%): C, 62.60; H, 4.24; Calcd (%) for C$_{30}$H$_{23}$PS$_5$: C, 62.69; H, 4.03.

Compound 23 [C$_6$H$_4$PhP(O)-DTE] Yield: 52%. $^1$H NMR (500 MHz, [D$_6$]acetone, 298 K): Conformer A δ 1.87 (s, 3H, —CH$_3$), 1.91 (s, 3H, —CH$_3$), 2.27 (s, 3H, —CH$_3$), 2.47 (s, 3H, —CH$_3$), 6.71 (s, 1H, thienyl), 6.87 (s, 1H, thienyl), 7.32-7.37 (m, 2H, phenyl), 7.43-7.50 (m, 3H, phenyl), 7.56-7.60 (m, 3H, phenyl), 7.61-7.64 (m, 1H, phenyl). Conformer B δ 1.80 (s, 3H, —CH$_3$), 2.13 (s, 3H, —CH$_3$), 2.23 (s, 3H, —CH$_3$), 2.40 (s, 3H, —CH$_3$), 6.36 (s, 1H, thienyl), 6.55 (s, 1H, thienyl), 7.40-7.43 (m, 2H, phenyl), 7.48-7.52 (m, 2H, phenyl), 7.65-7.70 (m, 3H, phenyl), 7.72-7.74 (m, 2H, phenyl). $^{31}$P{$^1$H} NMR (162 MHz, CDCl$_3$, 298 K): δ 35.31, 35.14. Positive EI-MS, m/z: 446. HRMS (Positive EI) calcd for C$_{26}$H$_{23}$OP$^{32}$S$_2$: m/z=446.0928. found: 446.0923 [M]$^+$. Elemental analyses. Found (%): C, 69.83; H, 5.16; Calcd (%) for C$_{26}$H$_{23}$OPS$_2$: C, 69.93; H, 5.19.

Compound 24 [C$_6$H$_4$(OMe)P(O)-DTE] Yield: 6-8%. NMR (500 MHz, [D$_6$]acetone, 358 K): Conformer A δ 1.88 (s, 3H, —CH$_3$), 1.97 (s, 3H, —CH$_3$), 2.37 (s, 3H, —CH$_3$), 2.46 (s, 3H, —CH$_3$), 3.60 (d, J=12 Hz, 3H, —OMe), 6.78 (s, 1H, thienyl), 6.81 (s, 1H, thienyl), 7.27-7.29 (m, 1H, phenyl), 7.47-7.51 (m, 1H, phenyl), 7.55-7.59 (m, 1H, phenyl), 7.71-7.75 (m, 1H, phenyl). Conformer B δ 1.92 (s, 3H, —CH$_3$), 2.07 (s, 3H, —CH$_3$), 2.37 (s, 3H, —CH$_3$), 2.40 (s, 3H, —CH$_3$), 3.70 (d, J=12 Hz, 3H, —OMe), 6.54 (s, 1H, thienyl), 6.77 (s, 1H, thienyl), 7.24-7.27 (m, 1H, phenyl), 7.47-7.51 (m, 1H, phenyl), 7.55-7.59 (m, 1H, phenyl), 7.71-7.75 (m, 1H, phenyl). $^{31}$P{$^1$H} NMR (162 MHz, [D$_6$] acetone, 298 K): δ 44.15, 44.26. Positive EI-MS, m/z: 400. HRMS (Positive EI) calcd for C$_{21}$H$_{21}$O$_2$P$^{32}$S$_2$: m/z=400.0721. found: 400.0718 [M]$^+$. Elemental analyses. Found (%): C, 62.66; H, 5.37; Calcd (%) for C$_{21}$H$_{21}$O$_2$PS$_2$: C, 62.98; H, 5.29.

Compound 25 [C$_6$H$_4$ThPhP(O)-DTE] Yield: 9-11%. $^1$H NMR (400 MHz, [D$_6$]DMSO, 358 K): δ 1.85 (s, 3H, —CH$_3$), 2.00 (s, 3H, —CH$_3$), 2.29 (s, 3H, —CH$_3$), 2.46 (s, 3H, —CH$_3$), 6.57 (s, 1H, thienyl), 6.94 (s, 1H, thienyl), 7.38-7.43 (m, 2H, phenyl), 7.45-7.50 (m, 2H, phenyl), 7.55-7.58 (m, 1H, phenyl), 7.64-7.73 (m, 3H, phenyl), 8.06-8.08 (m, 1H, phenyl). $^{31}$P{$^1$H} NMR (162 MHz, [D$_6$] DMSO, 298 K): 28.97. Positive EI-MS, m/z: 502. HRMS (Positive EI) calcd for C$_{28}$H$_{23}$OP$^{32}$S$_3$: m/z=502.0649. found: 502.0638 [M]$^+$. Elemental analyses. Found (%): C, 65.48; H, 4.45; Calcd (%) for C$_{28}$H$_{23}$OPS$_3$.0.5H$_2$O: C, 65.73; H, 4.73.

Compound 26 [TThPhP(O)-DTE] Yield: 9-11%. $^1$H NMR (400 MHz, [D$_6$]DMSO, 358 K): δ 1.84 (s, 3H, —CH$_3$), 2.00 (s, 3H, —CH$_3$), 2.28 (s, 3H, —CH$_3$), 2.44 (s, 3H, —CH$_3$), 6.54 (s, 1H, thienyl), 6.91 (s, 1H, thienyl), 7.47-7.54 (m, 3H, phenyl and thienyl), 7.57-7.60 (m, 1H, thienyl), 7.64-7.70 (m, 3H, phenyl). $^{31}$P{$^1$H} NMR (162 MHz, [D$_6$]DMSO, 298 K): δ 25.83. Positive EI-MS, m/z: 508. HRMS (Positive EI) calcd for C$_{26}$H$_{21}$OP$^{32}$S$_4$: m/z=508.0213. found: 508.0200 [M]$^+$. Elemental analyses. Found (%): C, 60.73; H, 4.17; Calcd (%) for C$_{26}$H$_{21}$OPS$_4$.0.5MeOH: C, 60.66; H, 4.42.

Compound 27 [C$_6$H$_4$TThPhP(O)-DTE] Yield: 7-9%. $^1$H NMR (400 MHz, [D$_6$]DMSO, 358 K): δ 1.68 (s, 3H, —CH$_3$), 2.20 (s, 3H, —CH$_3$), 2.29 (s, 3H, —CH$_3$), 2.47 (s, 3H, —CH$_3$), 6.57 (s, 1H, thienyl), 6.98 (s, 1H, thienyl), 7.42-7.45 (m, 1H, phenyl), 7.48-7.53 (m, 3H, phenyl), 7.58-7.61 (m, 1H, phenyl), 7.68-7.73 (m, 2H, phenyl), 8.00-8.05 (m, 2H, phenyl). $^{31}$P{$^1$H} NMR (162 MHz, [D$_6$] DMSO, 298 K): δ 25.68. Positive EI-MS, m/z: 558. HRMS (Positive EI) calcd for C$_{30}$H$_{23}$OP$^{32}$S$_4$: m/z=558.0366. found: 558.0369 [M]$^+$. Elemental analyses. Found (%): C, 64.64; H, 4.20; Calcd (%) for C$_{30}$H$_{23}$OPS$_4$: C, 64.49; H, 4.15.

Compound 28 [C$_6$H$_4$TThPhP(O)-DT(NPh$_2$)E] Yield: 14%. $^1$H NMR (400 MHz, [D$_6$]DMSO, 358 K): δ 2.06 (s, 3H, —CH$_3$), 2.16 (s, 3H, —CH$_3$), 6.41 (s, 1H, thienyl), 6.86 (s, 1H, thienyl), 6.94-6.97 (m, 4H, phenyl), 7.03-7.07 (m, 3H, phenyl), 7.09-7.12 (m, 5H, phenyl), 7.26-7.29 (m, 4H, phenyl), 7.32-7.36 (m, 4H, phenyl), 7.42-7.53 (m, 4H, phenyl), 7.58-7.62 (m, 1H, phenyl), 7.65-7.71 (m, 2H, phenyl), 8.00-8.05 (m, 2H, phenyl). $^{31}$P{$^1$H} NMR (162 MHz, [D$_6$]DMSO, 298 K): δ 25.97. Positive EI-MS, m/z: 864. HRMS (Positive EI) calcd for C$_{52}$H$_{37}$ON$_2$P$^{32}$S$_4$: m/z=864.1526. found: 864.1512 [M]$^+$. Elemental analyses. Found (%): C, 71.95; H, 4.76; N, 3.18; Calcd (%) for C$_{52}$H$_{37}$ON$_2$PS$_4$: C, 71.57; H, 4.46; N, 3.18.

Compound 29 [C$_6$H$_4$PhP-DTE] Yield: 59%. $^1$H NMR (500 MHz, [D$_6$]acetone, 298 K): Conformer A δ 1.86 (s, 3H, —CH$_3$), 1.96 (s, 3H, —CH$_3$), 2.28 (s, 3H, —CH$_3$), 2.48 (s, 3H, —CH$_3$), 6.54 (s, 1H, thienyl), 6.85 (s, 1H, thienyl), 7.23-7.26 (m, 2H, phenyl), 7.28-7.34 (m, 5H, phenyl), 7.41-7.45 (m, 2H, phenyl). Conformer B δ 1.88 (s, 3H, —CH$_3$), 2.22 (s, 3H, —CH$_3$), 2.26 (s, 3H, —CH$_3$), 2.35 (s, 3H, —CH$_3$), 6.34 (s, 1H, thienyl), 6.41 (s, 1H, thienyl), 7.28-7.34 (m, 2H, phenyl), 7.41-7.45 (m, 2H, phenyl), 7.66-7.70 (m, 2H, phenyl). $^{31}$P{$^1$H} NMR (162 MHz, CDCl$_3$, 298 K): δ 3.50, 3.10. Positive EI-MS, m/z: 430. HRMS (Positive EI) calcd for C$_{26}$H$_{23}$P$^{32}$S$_2$: m/z=430.0979. found: 430.0966 [M]$^+$. Elemental analyses. Found (%): C, 69.61; H, 5.49; Calcd (%) for C$_{26}$H$_{23}$PS$_2$.H$_2$O: C, 69.62; H, 5.62.

Compound 30 [C$_6$H$_4$PhP(S)-DTE] Yield: 63%. $^1$H NMR (500 MHz, CDCl$_3$, 298 K): Conformer A δ 1.61 (s, 3H, —CH$_3$), 1.96 (s, 3H, —CH$_3$), 2.33 (s, 3H, —CH$_3$), 2.44 (s, 3H, —CH$_3$), 6.64 (s, 1H, thienyl), 7.05 (s, 1H, thienyl), 7.32-7.37 (m, 3H, phenyl), 7.37-7.43 (m, 1H, phenyl), 7.48-7.51 (m, 3H, phenyl), 7.64-7.72 (m, 2H, phenyl). Conformer B δ 1.72 (s, 3H, —CH$_3$), 2.03 (s, 3H, —CH$_3$), 2.55 (s, 3H, —CH$_3$), 2.42 (s, 3H, —CH$_3$), 6.22 (s, 1H, thienyl), 6.51 (s, 1H, thienyl), 7.37-7.43 (m, 5H, phenyl), 7.64-7.72 (m, 2H, phenyl), 7.79-7.84 (m, 2H, phenyl). $^{31}$P{$^1$H} NMR (162 MHz, CDCl$_3$, 298 K): δ 47.29, 47.46. Positive EI-MS, m/z: 462. HRMS (Positive EI) calcd for C$_{26}$H$_{23}$P$^{32}$S$_3$: m/z=462.0699. found: 462.0678 [M]$^+$. Elemental analyses. Found (%): C, 67.67; H, 5.04; Calcd (%) for C$_{26}$H$_{23}$PS$_3$: C, 67.50; H, 5.01.

Compound 31 [C$_6$H$_4$PhP(Se)-DTE] Yield: 79%. $^1$H NMR (500 MHz, [D$_6$]acetone, 298 K): Conformer A δ 1.70 (s, 3H, —CH$_3$), 1.97 (s, 3H, —CH$_3$), 2.31 (s, 3H, —CH$_3$), 2.45 (s, 3H, —CH$_3$), 6.86 (s, 1H, thienyl), 7.22 (s, 1H, thienyl), 7.50-7.54 (m, 5H, phenyl), 7.64-7.68 (m, 2H, phenyl), 7.84-7.86 (m, 2H, phenyl). Conformer B δ 1.77 (s, 3H, —CH$_3$), 2.09 (s, 3H, —CH$_3$), 2.23 (s, 3H, —CH$_3$), 2.42 (s, 3H, —CH$_3$), 6.28 (s, 1H, thienyl), 6.63 (s, 1H, thienyl), 7.39-7.46 (m, 4H, phenyl), 7.59-7.65 (m, 3H, phenyl), 7.76-7.81 (m, 2H, pheny). $^{31}$P {$^1$H} NMR (162 MHz, [D$_6$]acetone, 298 K): δ 35.29, 36.33. Positive EI-MS, m/z: 510. HRMS (Positive EI) calcd for C$_{26}$H$_{23}$P$^{32}$S$_2$$^{80}$Se: m/z=510.0144. found: 510.0199 [M]$^+$. Elemental analyses. Found (%): C, 60.22; H, 4.55; Calcd (%) for C$_{26}$H$_{23}$PS$_2$Se.0.5H$_2$O: C, 60.23; H, 4.67.

Compound 32 {[C$_6$H$_4$PhP(SMe)-DTE](OTf)} Yield: 86%. $^1$H NMR (500 MHz, [D$_6$]acetone, 298 K): Conformer A δ 1.75 (s, 3H, —CH$_3$), 2.07 (s, 3H, —CH$_3$), 2.43 (s, 3H, —CH$_3$), 2.47 (s, 3H, —CH$_3$), 2.62 (d, J=16 MHz, 3H, —SMe), 6.95 (s, 1H, thienyl), 7.07 (s, 1H, thienyl), 7.72-7.80 (m, 3H, phenyl), 7.86-7.94 (m, 2H, phenyl), 8.01-8.03 (m, 3H, phenyl), 8.37-8.40 (m, 1H, phenyl). Conformer B δ 1.83 (s, 3H, —CH$_3$), 2.11 (s, 3H, —CH$_3$), 2.33 (s, 3H, —CH$_3$), 2.44 (s, 3H, —CH$_3$), 2.54 (d, J=16 MHz, 3H, —SMe), 6.47 (s, 1H, thienyl), 6.84 (s, 1H, thienyl), 7.72-7.80 (m, 2H, phenyl), 7.82-7.90 (m, 5H, phenyl), 7.99-8.01 (m, 1H, phenyl), 8.28-8.32 (m, 1H, phenyl). $^{31}$P{$^1$H} NMR (162 MHz, [D$_6$]acetone, 298 K): δ 49.43, 49.87. Positive FAB-MS, m/z: 477 [M]$^+$. Elemental analyses. Found (%): C, 51.42; H, 4.08; Calcd (%) for C$_{28}$H$_{28}$F$_3$O$_4$PS$_3$.0.5CH$_2$Cl$_2$: C, 51.15; H, 4.07.

Compound 33 [C$_6$H$_4$PhP(AuCl)Th-DTE] Yield: 43%. $^1$H NMR (400 MHz, [D$_6$]DMSO, 353 K): δ 1.69 (s, 3H, —CH$_3$), 2.20 (s, 3H, —CH$_3$), 2.32 (s, 6H, —CH$_3$), 6.54 (s, 2H, thienyl), 7.30-7.35 (m, 2H, phenyl), 7.43-7.47 (m, 2H, phenyl), 7.49-7.51 (m, 1H, phenyl), 7.53-7.58 (m, 1H, phenyl), 7.68-7.72 (m, 1H, phenyl), 7.85-7.90 (m, 2H, phenyl). $^{31}$P{$^1$H} NMR (162 MHz, [D$_6$]DMSO, 298 K): δ 15.81. Positive FAB-MS, m/z: 718 [M]$^+$.

Photochromic Properties

A solution sample of the compound was degassed on a high vacuum line in a degassing cell with a 10 cm$^3$ Pyrex round-bottom flask connected by a side-arm to a 1-cm quartz fluorescence cuvette and was sealed from the atmosphere by a Rotaflo HP6/6 quick-release Teflon stopper. The solution samples were rigorously degassed with no fewer than four freeze-pump-thaw cycles prior to the measurements.

Figure 2:
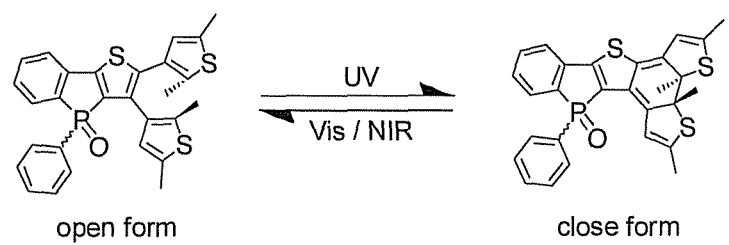
FIG. 2 shows the photochromic reaction of compound 12.
Figure 3:
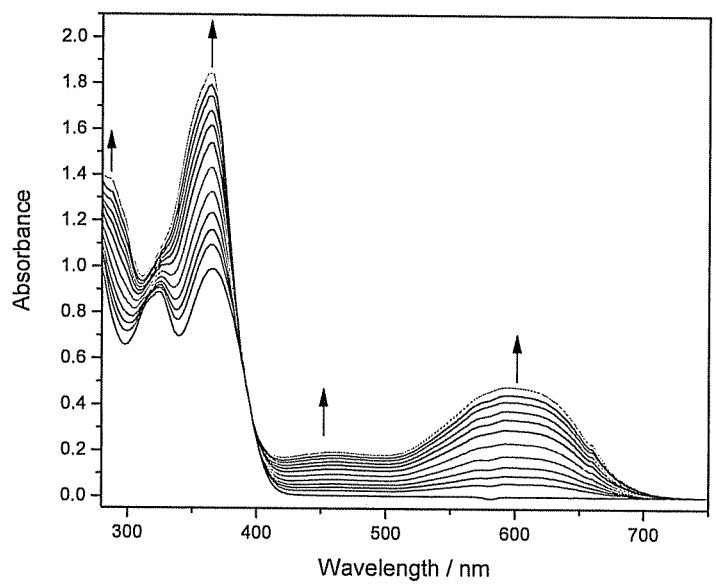
FIG. 3 shows the UV-vis absorption spectral changes of 12 in degassed benzene upon excitation at 391 nm.
Figure 4:
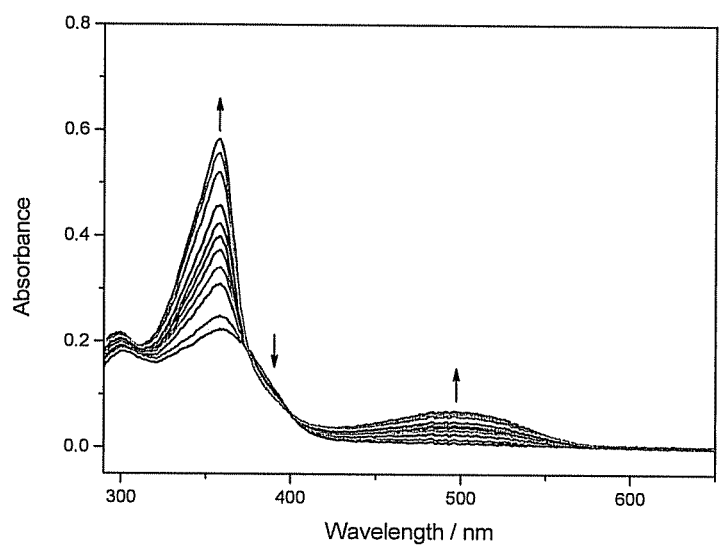
FIG. 4 shows the UV-vis absorption spectral changes of 23 in degassed benzene upon excitation at 360 nm.
Figure 5:
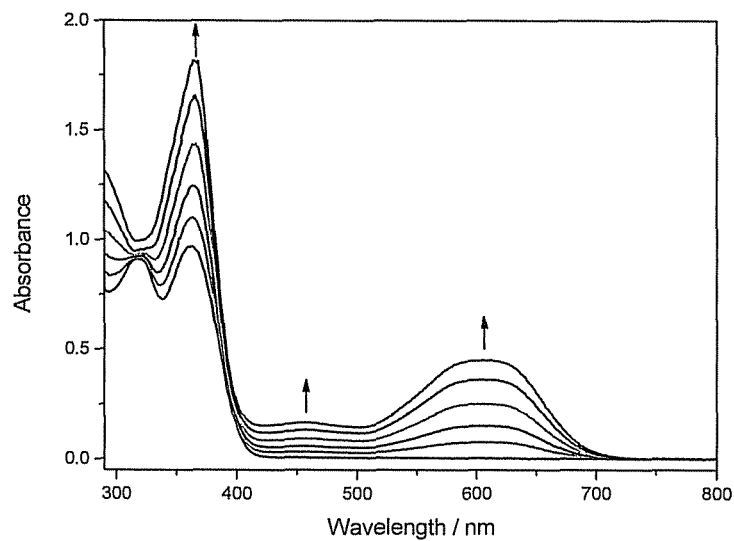
FIG. 5 shows the UV-vis absorption spectral changes of 33 in degassed benzene upon excitation at 360 nm.
Figure 6:
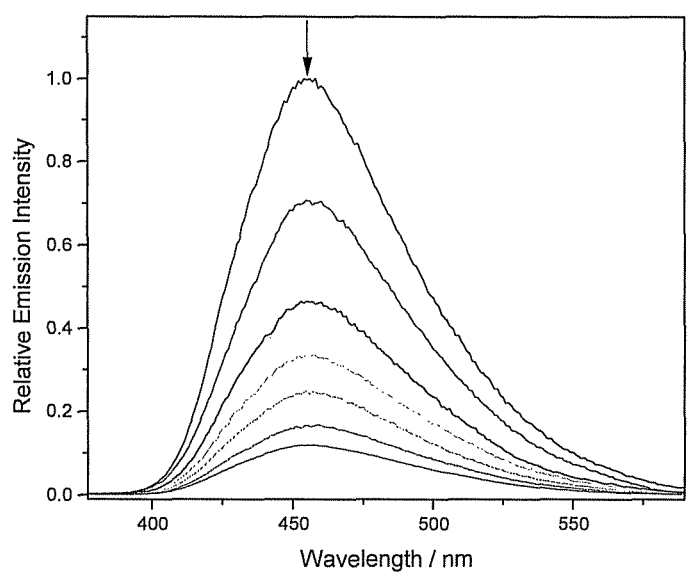
FIG. 6 shows the emission spectral changes of 12 in degassed benzene upon excitation at 391 nm.

The solution sample was irradiated at the UV absorption band, whereby the initial colorless to pale yellow solution turned into deep-colored solution. The colored state was thermally very stable. Then, it was irradiated with visible light, whereby the solution was decolorized. The UV-vis absorbance changes of the compounds were capable of undergoing repeated reversible changes. FIG. 1 shows the UV-vis absorption spectral changes of 1 in degassed benzene upon excitation at 362 nm. FIG. 2 shows the photochromic reaction of compound 12 and FIG. 3 shows the UV-vis absorption spectral changes of 12 in degassed benzene upon excitation at 391 nm. FIG. 4 show the UV-vis absorption spectral changes of 23 in degassed benzene upon excitation at 360 nm. FIG. 5 show the UV-vis absorption spectral changes of 33 in degassed benzene upon excitation at 360 nm. The electronic absorption data of the open forms and closed forms are summarized in Table 1. Besides the UV-vis spectral change, the emission intensity would decrease upon photocyclization of the phosphole compounds (FIG. 6), rendering the compounds possible photoswitchable materials. The quantum yields for both photocyclization and photo-cycloreversion of the photochromic compounds are summarized in Table 2. The conversion at photostationary state is also summarized in Table 2.

TABLE 1

Electronic absorption data for the compounds in benzene solution at 298K

| Compound | Configuration | Absorption $\lambda_{max}$/nm ($\varepsilon$/dm$^3$mol$^{-1}$cm$^{-1}$) |
|---|---|---|
| 1 | Open form | 330 (6470) |
|   | Closed form | 332sh (22200), 342 (26250), 475 (4490) |
| 4 | Open form | 296 (8680), 343 (5530) |
|   | Closed form | 340 (27760), 477 (4000) |
| 6 | Open form | 360 (5220) |
|   | Closed form | 342 (24600), 444 (5600) |
| 8 | Open form | 334 (6470), 371 (8820) |
|   | Closed form | 343 (25800), 359 (38790), 474 (4470) |
| 9 | Open form | 299 (25160), 350sh (4620), 378sh (2470) |
|   | Closed form | 319 (24400), 341sh (20660), 440 (3860) |
| 11 | Open form | 308 (10640), 318 (10640), 333 (9240), 385 (17820) |
|   | Closed form | 352 (29070), 371 (34630), 472 (7210), 498sh (6100) |
| 12 | Open form | 324 (8870), 365 (9860) |
|   | Closed form | 288 (19870), 363 (29750), 426 (3790), 600 (9390) |
| 13 | Open form | 308 (6750), 378 (9050) |
|   | Closed form | 294 (16250), 369 (18000), 477 (2810), 629 (5010) |
| 14 | Open form | 325 (8380), 376 (10850) |
|   | Closed form | 292 (21450), 372 (25900), 470 (4390), 623 (8250) |
| 15 | Open form | 327 (6690), 366 (6790) |
|   | Closed form | 288 (10140), 364 (16700), 460 (1740), 587 (4550) |
| 16 | Open form | 333 (10630), 376 (7970) |
|   | Closed form | 288 (10780), 369 (23910), 459 (2110), 582 (5390) |
| 17 | Open form | 304 (12990), 364 (9780) |
|   | Closed form | 365 (23900), 457 (3180), 602 (8390) |
| 18 | Open form | 321 (7160), 351 (9050) |
|   | Closed form | 361 (22970), 592 (9440) |
| 19 | Open form | 328 (12100) |
|   | Closed form | 357 (24000), 573 (9170) |
| 20 | Open form | 310 (4580), 376 (4200) |
|   | Closed form | 295 (11433), 371 (13180), 460 (2200), 631 (3830) |
| 21 | Open form | 324 (10180), 363 (6950) |
|   | Closed form | 314 (12080), 357 (15690), 559 (5910) |
| 22 | Open form | 314 (19120), 382 (15660) |
|   | Closed form | 316 (17350), 376 (19900), 453sh (2750), 572sh (3410), 591 (3540) |

TABLE 1-continued

Electronic absorption data for the compounds in benzene solution at 298K

| Compound | Configuration | Absorption $\lambda_{max}$/nm ($\varepsilon$/dm$^3$mol$^{-1}$cm$^{-1}$) |
|---|---|---|
| 23 | Open form | 360 (5560) |
|    | Closed form | 357 (31900), 499 (5050) |
| 25 | Open form | 333 (8090), 408 (7030) |
|    | Closed form | 357sh (31800), 371 (47600), 486 (5910) |
| 31 | Open form | 354 (7700) |
|    | Closed form | 360 (26700), 502 (3730) |
| 32 | Open form | 358 (6520) |
|    | Closed form | 360 (30300), 381 (25700), 448 (5850), 519 (4960) |
| 33 | Open form | 317 (9750), 362 (10400) |
|    | Closed form | 367 (34500), 458 (4560), 608 (12700) |
|    |             | 367 (34500), 458 (4560), 608 (12700) |

TABLE 2

Photochemical quantum yields and conversion at photostationary state determined in degassed benzene solution at 298K

| Compound | Photochemical Quantum Yield/$\phi^a$ | | Conversion at PSS (%) |
|---|---|---|---|
|   | Photocyclization | Photocycloreversion | |
| 1 | 0.39[b] | 0.27[c] | 44 |
| 4 | 0.32[b] | 0.31[c] | 44 |
| 6 | 0.19[b] | 0.20[c] | 53 |
| 8 | 0.48[b] | 0.42[c] | 66 |
| 9 | 0.42[b] | 0.36[c] | 67 |
| 11 | 0.32[b] | 0.19[c] | 80 |
| 12 | 0.28[b] | 0.03[d] | 49 |
| 13 | 0.45[b] | 0.023[d] | 87 |
| 14 | 0.23[b] | 0.014[d] | 60 |
| 15 | 0.50[b] | 0.057[d] | 62 |
| 16 | 0.37[b] | 0.063[d] | 63 |
| 17 | 0.37[b] | 0.026[d] | 69 |
| 18 | 0.34[b] | 0.027[d] | 46 |
| 19 | 0.43[b] | 0.021[d] | 53 |
| 20 | 0.17[b] | 0.048[d] | 37 |
| 21 | 0.26[b] | 0.097[d] | 39 |
| 22 | 0.08[b] | 0.092[d] | 85 |
| 23 | 0.64[b] | 0.24[e] | 34 |
| 25 | 0.52[b] | 0.21[e] | 83 |
| 31 | 0.65[b] | 0.29[e] | 59 |
| 32 | 0.20[b] | 0.074[e] | 49 |
| 33 | 0.18[b] | 0.01[e] | 38 |

[a]Data obtained with an uncertainty of ±10%
[b]Data obtained using 334 nm as the excitation source
[c]Data obtained using 468 nm as the excitation source
[d]Data obtained using 509 nm as the excitation source
[e]Data obtained using 500 nm as the excitation source Example 2

Figure 7:
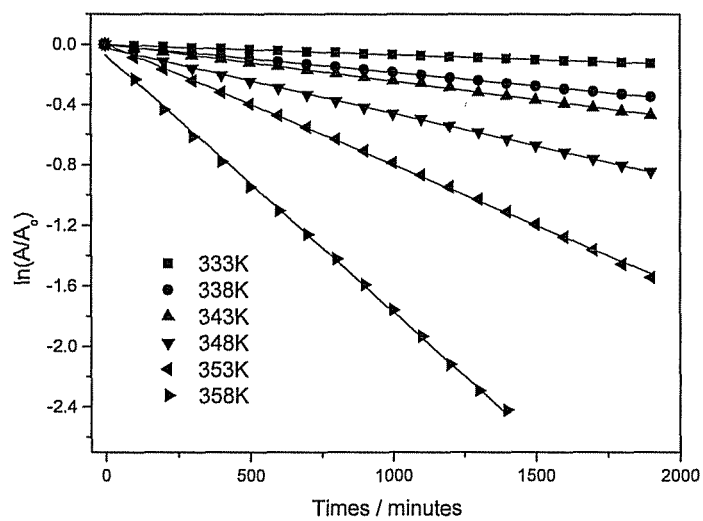
FIG. 7 shows a plot of $\ln(A/A_o)$ versus time for the absorbance decay of 12 at 638 nm at various temperatures in argon-flushed toluene solution; A denotes absorbance at time t and $A_o$ denotes the initial absorbance; solid lines represent the theoretical linear fits.
Figure 8:
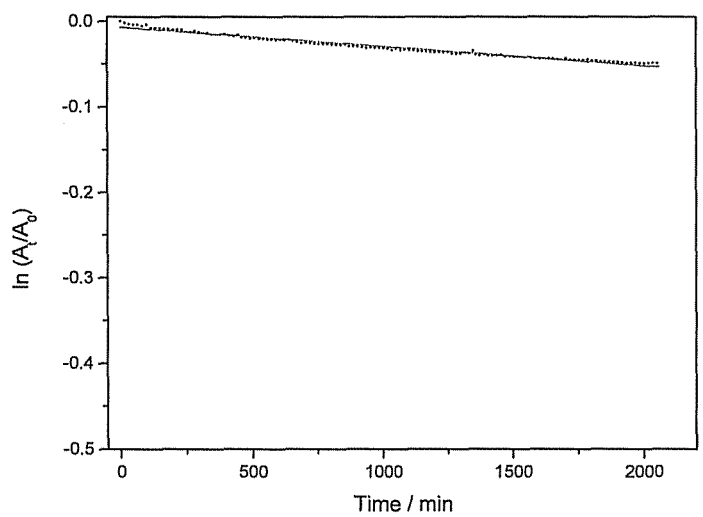
FIG. 8 shows a plot of $\ln(A/A_o)$ versus time for the absorbance decay of 25 at 500 nm at 358 K in argon-flushed decahydronaphthalene solution; A denotes absorbance at time t and $A_o$ denotes the initial absorbance.
Figure 9:
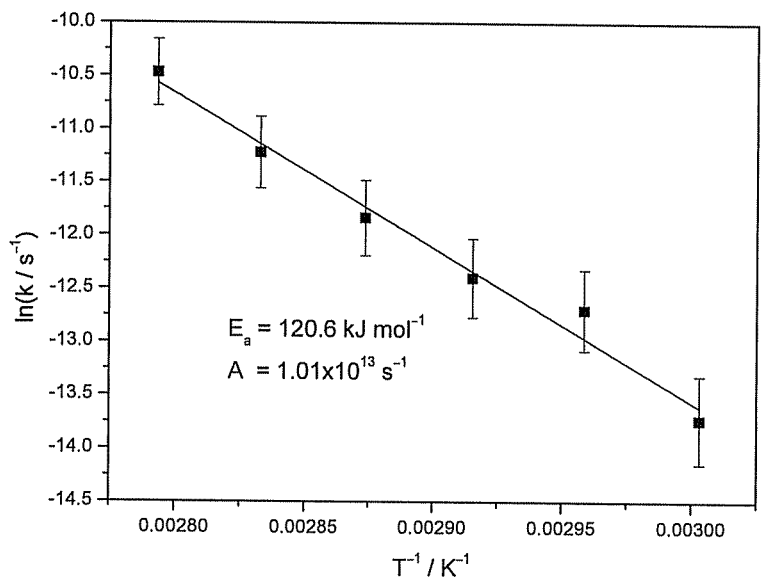
FIG. 9 shows the Arrhenius plot for the thermal backward reaction of the closed form of 12 in argon-flushed toluene solution.

Compound 12 was used to demonstrate the thermal stability of the closed form of the photochromic compounds by measuring the absorbance decay at different temperatures in the dark (FIG. 7). Compound 25 was also selected to investigate the thermal stability at 358 K (FIG. 8). By plotting the rates of thermal backward reaction at different temperature against the temperature, the Arrhenius plot (FIG. 9) could be obtained, which could be used to determine the activation energy (120.6 kJ mol$^{-1}$) and the pre-exponential factor (1.01×10$^{13}$ s$^{-1}$) of the thermal cycloreversion of compound 12.

Example 3

Figure 10:
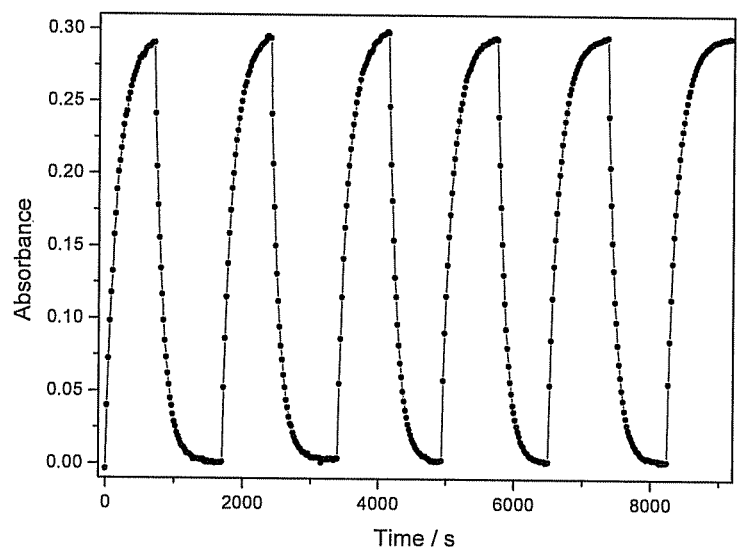
FIG. 10 shows the UV-vis absorbance changes of 6 at 444 nm on alternate excitation at 380 and 444 nm over five cycles in degassed benzene solution at 298 K.
Figure 11:
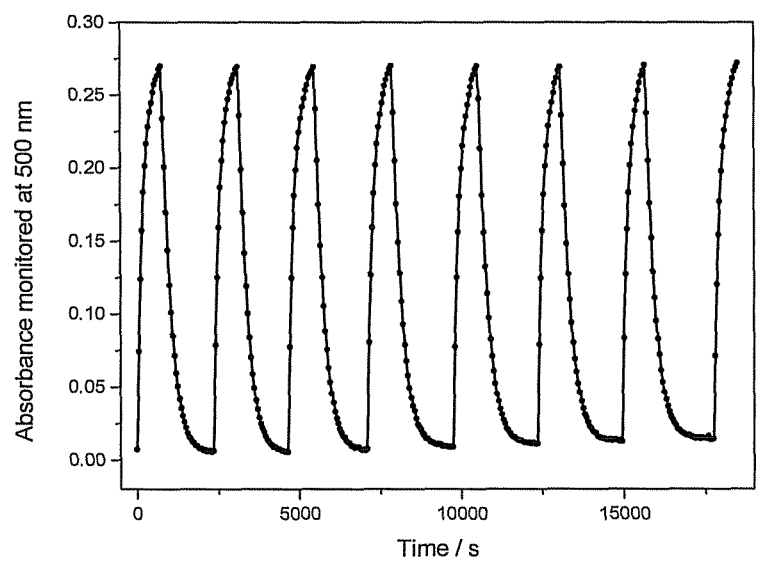
FIG. 11 shows the UV-vis absorbance changes of 23 at 500 nm on alternate excitation at 360 and 500 nm over seven cycles in degassed benzene solution at 298 K.

Fatigue resistance represents another important parameter commonly used to evaluate the performance of photochromic materials. Photochromic materials could lose their photochromic reactivities though side-reactions of the closed form. The fatigue resistance of the compound could be demonstrated by alternate excitation at the absorption bands of the open form and the closed form of the compounds and monitoring the UV-vis absorption changes at a selected wavelength. Compound 6 and 23 were used to demonstrate the fatigue resistance of the photochromic compounds, as depicted in FIGS. 10 and 11, respectively.

Example 4

Photochromic properties of compounds 2 and 12 in solid thin film were studied by dissolving 80 mg of PMMA and the compound (25 mg of 2 or 15 mg of 12) into 1 mL of chloroform. Then it was spin-coated on a quartz plate (20 mm×20 mm×1 mm) with a spin rotation speed of 2000 rpm on a Laurell Technologies Corporation Single Wafer Spin Processor (Model: WS-400A6TFM/LITE). With the use of a mask, the quartz plate is able to be recorded with different patterns by undergoing a color change and it is stable in the dark for a period of time.

Those skilled in the art will recognize that various changes and modifications can be made in the invention without departing from the spirit and scope thereof. The various embodiments described were for the purpose of further illustrating the invention and were not intended to limit it.

What is claimed is:

1. A photochromic compound comprising a diarylethene, in which an ethene moiety forms part of a mono- or poly-cyclic ring structure with at least one of a silicon-containing heterocycle or a phosphorus-containing heterocycle, which comprises a butadiene or a hexatriene moiety to form a conjugated aromatic heterocycle, the photochromic compound having the chemical structure

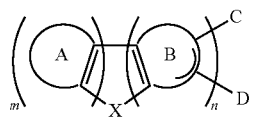

(I)

wherein:
X comprises silicon or phosphorus;
A and B are cyclic structure derivatives, m and n are the number of rings in the cyclic structure derivatives and m and n are independently greater than or equal to zero;
C and D are heterocyclic groups that are cyclizable by irradiation with light to form a cyclohexadiene ring for tuning the optical properties.

2. The photochromic compound according to claim 1, wherein X is one or more of SiRR', P(O)R, P(BH$_3$)R, P(BL$_3$)R, P(S)R, P(Se)R, P(CH$_3$)R, P(SR')R, PR, P(R')R, P(WL$_5$)R, P(CrL$_5$)R, P(MnL$_5$)R, P(MoL$_5$)R, P(ReL$_5$)R, P(PtL$_3$)R, P(PdL$_3$)R, P(CuL$_3$)R, P(CuL)R, P(RuL$_5$)R, P(IrL$_5$)R, P(FeL$_4$)R, P(RhL$_3$)R, P(RhL$_5$)R, P(CoL$_3$)R, P(NiL$_3$)R, P(AgL)R, P(AgL$_3$)R, P(AuL)R, or P(AuL)R' where R, R' or L is independently alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

3. The photochromic compound according to claim 2, wherein the X is P(CH$_3$)R or P(R')R, and wherein P(CH$_3$)R or P(R')R have a counter-anion: OTf$^-$, PF$_6^-$, BF$_4^-$, BPh$_4^-$, ClO$_4^-$ or halide ions, where R and R' are independently alkyl, alkenyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfhydryl, sulfinyl, halo, aryl, substituted aryl, heteroaryl, substituted heteroaryl or a heterocyclic group.

4. The photochromic compound according to claim 1, wherein rings A and B are cyclic structure derivatives where the cyclic structures are independently selected from a 5- or 6-membered arene, heteroacene or heterocycle, the arene, heteroacene or heterocycle selected from benzene, pyridine, thiophene, furan, pyrazole, imidazole, oxazole, isoxazole, thiazole, isothiazole, isoquioline, pyrrole, pyrazine, pyridazine, pyrimidine, benzimidazole, benzofuran, benzothiazole, indole, naphthalene, anthracene, pyrene, triazole, tetrazole, pyran, thiapyran, oxadiazole, triazine, tetrazine, carbazole, dibenzothiophene, dibenzofuran, fluorene, or derivatives thereof.

5. The photochromic compound according to claim 1, wherein rings A and B are unsubstituted or substituted with one or more alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group, and additionally, or alternatively, any two adjacent substituted positions of rings A and B together form, independently, a fused 5- or 6-membered cyclic group, wherein the said cyclic group is cycloalkyl, cycloheteroalkyl, aryl, or heteroaryl, and wherein the fused 5- to 6-membered cyclic group is substituted with one or more of alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, phosphate, pyridyl, sulfonyl, sulfo, sulfinyl, sulfhydryl, halo, aryl, substituted aryl, heteroaryl, substituted heteroaryl or a heterocyclic group.

6. The photochromic compound according to claim 1, wherein the heterocyclic group for C and D in the formula (I), has the formula (II) or (III):

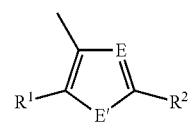

(II)

wherein
E is C, R$^3$ or N;
E' comprises at least one heteroatom, selected from S, SO$_2$, O, Se and NR$^4$;
R$^1$ is an alkyl group, alkoxy group, halogen atom or trifluoromethyl group, R$^2$ and R$^3$ are each independently an atom or group selected from the group of hydrogen atom, halogen atom, hydroxyl group, alkyl group, alkynyl group, alkoxy group, cyano group, nitro group, alkylcarbonyl group, alkoxycarbonyl group, perfluoroalkyl group, aryl group, cycloalkyl group, arylcarbonyl group, aryloxycarbonyl group, diarylamino group, dialkylamino group, mono- or dialkylaminocarbonyl group, alkylcarbonyloxy group, arylcarbonyloxy group, aryloxy group, alkoxycarbonyl group, and aryloxycarbonyloxy group, and $R^4$ is a hydrogen atom or a substituted or unsubstituted alkyl, aryl or cycloalkyl group;

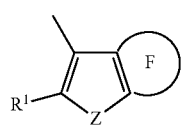
(III)

wherein:
Z comprises at least one heteroatom; and
$R^1$ is an alkyl group, alkoxy group, halogen atom or trifluoromethyl group, $R^4$ is a hydrogen atom or a substituted or unsubstituted alkyl, aryl or cycloalkyl group;
Ring F comprises cyclic structure derivatives where the cyclic structures are independently selected from a 5- or 6-membered arene, heteroacene or heterocycle, the arene, heteroacene or heterocycle being one or more selected from benzene, pyridine, thiophene, furan, pyrazole, imidazole, oxazole, isoxazole, thiazole, isothiazole, isoquioline, pyrrole, pyrazine, pyridazine, pyrimidine, benzimidazole, benzofuran, benzothiazole, indole, naphthalene, anthracene, pyrene, triazole, tetrazole, pyran, thiapyran, oxadiazole, triazine, tetrazine, carbazole, dibenzothiophene, dibenzofuran, fluorene and derivatives thereof;
wherein
Ring F can be unsubstituted or substituted with one or more alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, pyridyl, sulfonyl, sulfo, sulfinyl, sulfhydryl, halo, aryl, substituted aryl, heteroaryl, substituted heteroaryl or a heterocyclic group, and additionally, or alternatively, any two adjacent substituted positions of ring F together form, independently, a fused 5- or 6-membered cyclic group, wherein the said cyclic group is cycloalkyl, cycloheteroalkyl, aryl, or heteroaryl, and wherein the fused 5- to 6-membered cyclic group may be substituted with one or more of alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, pyridyl, sulfonyl, sulfo, sulfinyl, sulfhydryl, halo, aryl, substituted aryl, heteroaryl, substituted heteroaryl or a heterocyclic group.

7. The photochromic compound of claim 1, wherein the compound has the chemical structure:

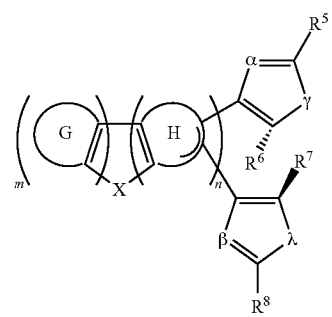

wherein:
G and H are cyclic structure derivatives;
m and n are the number of rings in the cyclic structure derivatives and they are greater than or equal to zero;
X comprises silicon or phosphorus;
α and β independently represent C—$R^9$ or N;
γ and λ independently comprise heteroatoms selected from S, $SO_2$, O, Se and $NR^{10}$;
$R^6$ and $R^7$ independently represent alkyl group, alkoxy group, halogen atom or trifluoromethyl group;
$R^5$, $R^8$ and $R^9$ are independently atoms or groups selected from the group of hydrogen atom, halogen atom, hydroxyl group, alkyl group, alkynyl group, alkoxy group, cyano group, nitro group, alkylcarbonyl group, alkoxycarbonyl group, perfluoroalkyl group, aryl group, cycloalkyl group, arylcarbonyl group, aryloxycarbonyl group, diarylamino group, dialkylamino group, mono- or dialkylaminocarbonyl group, alkylcaronyloxy group, arylcarbonyloxy group, aryloxy group, alkoxycarbonyl group, and aryloxycarbonyloxy group; and
$R^{10}$ is a hydrogen atom or a substituted or unsubstituted alkyl, aryl or cycloalkyl group.

8. A photochromic compound selected from one of

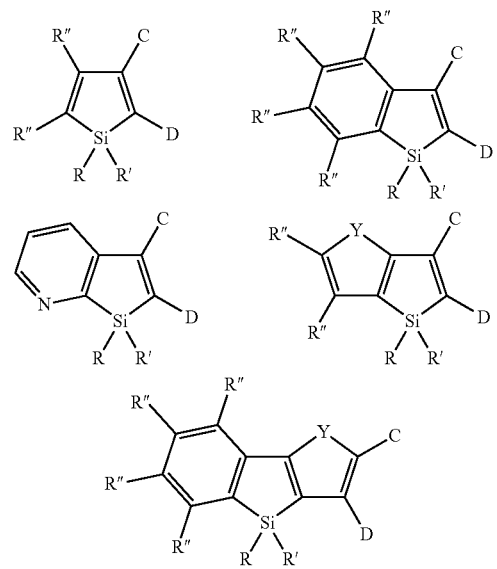

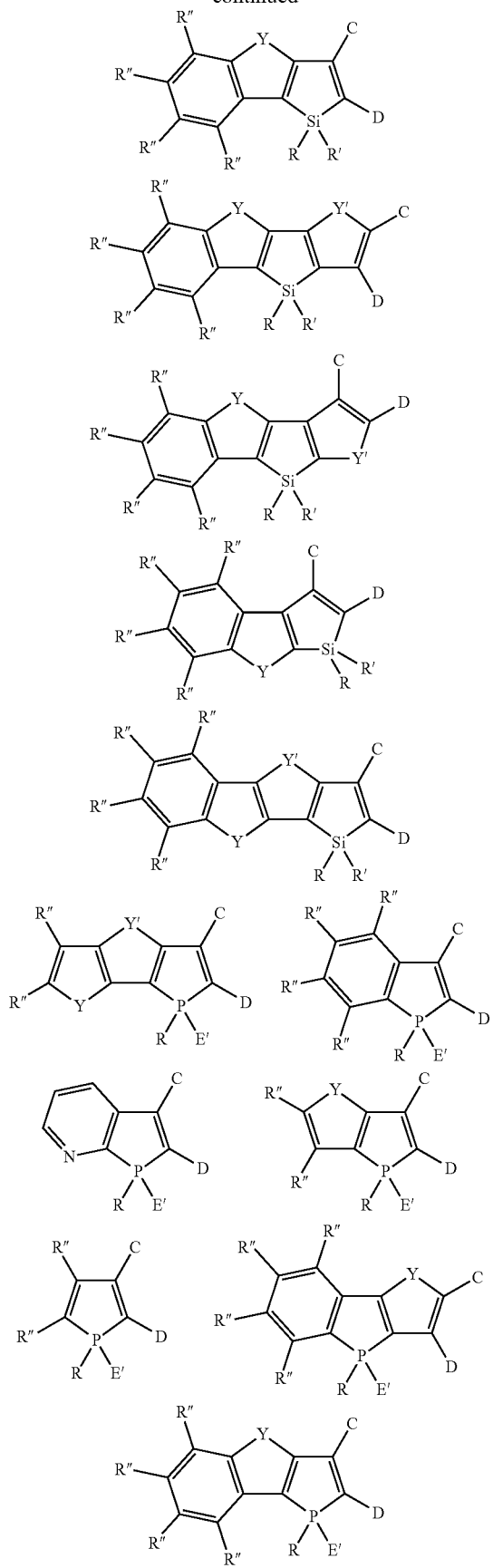

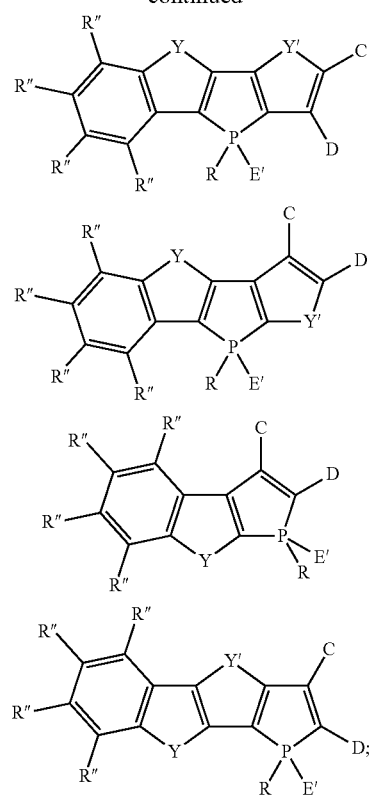

wherein

C and D are heterocyclic groups that are cyclizable by irradiation with light to form cyclohexadiene ring for tuning the optical properties, wherein C and D have the formula (IV) or (V):

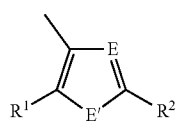

(IV)

wherein

E is C—R$^3$ or N;

E' comprises at least one heteroatom, selected from S, SO$_2$, O, Se and NR$^4$;

R$^1$ is an alkyl group, alkoxy group, halogen atom or trifluoromethyl group, R$^2$ and R$^3$ are independently an atoms or groups selected from the group of hydrogen atom, halogen atom, hydroxyl group, alkyl group, alkynyl group, alkoxy group, cyano group, nitro group, alkylcarbonyl group, alkoxycarbonyl group, perfluoroalkyl group, aryl group, cycloalkyl group, arylcarbonyl group, aryloxycarbonyl group, diarylamino group, dialkylamino group, mono- or dialkylaminocarbonyl group, alkylcarbonyloxy group, arylcarbonyloxy group, aryloxy group, alkoxycarbonyl group, and aryloxycarbonyloxy group, and R$^4$ is a hydrogen atom or a substituted or unsubstituted alkyl, aryl or cycloalkyl group;

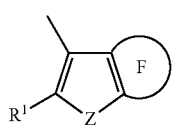

(V)

wherein:
- Z comprises at least one heteroatom selected from S, SO$_2$, O, Se and NR$^4$;
- R$^1$ is an alkyl group, alkoxy group, halogen atom or trifluoromethyl group, R$^4$ is a hydrogen atom or a substituted or unsubstituted alkyl, aryl or cycloalkyl group;
- Ring F comprises cyclic structure derivatives where the cyclic structures are independently selected from a 5- or 6-membered arene, heteroacene or heterocycle, the arene, heteroacene or heterocycle being one or more selected from benzene, pyridine, thiophene, furan, pyrazole, imidazole, oxazole, isoxazole, thiazole, isothiazole, isoquioline, pyrrole, pyrazine, pyridazine, pyrimidine, benzimidazole, benzofuran, benzothiazole, indole, naphthalene, anthracene, pyrene, triazole, tetrazole, pyran, thiapyran, oxadiazole, triazine, tetrazine, carbazole, dibenzothiophene, dibenzofuran, fluorene and derivatives thereof; and
- Ring F can be unsubstituted or can be substituted with one or more alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, pyridyl, sulfonyl, sulfo, sulfinyl, sulfhydryl, halo, aryl, substituted aryl, heteroaryl, substituted heteroaryl or a heterocyclic group, and additionally, or alternatively, any two adjacent substituted positions of ring F together form, independently, a fused 5- or 6-membered cyclic group, wherein the said cyclic group is cycloalkyl, cycloheteroalkyl, aryl, or heteroaryl, and wherein the fused 5- to 6-membered cyclic group may be substituted with one or more of alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketamine, isocyanate, isocyanide, isothiocyanate, nitrile, nitro, nitroso, phosphine, phosphate, phosphono, pyridyl, sulfonyl, sulfo, sulfinyl, sulfhydryl, halo, aryl, substituted aryl, heteroaryl, substituted heteroaryl or a heterocyclic group;
- R, R', R" are independently atoms or groups selected from the group of hydrogen atom, halogen atom, hydroxyl group, alkyl group, alkynyl group, alkoxy group, cyano group, nitro group, alkylcarbonyl group, alkoxycarbonyl group, perfluoroalkyl group, aryl group, cycloalkyl group, arylcarbonyl group, aryloxycarbonyl group, diarylamino group, dialkylamino group, mono- or dialkylaminocarbonyl group, alkylcaronyloxy group, arylcarbonyloxy group, aryloxy group, alkoxycarbonyl group, and aryloxycarbonyloxy group;
- E" refers to atoms or groups selected from O, BH$_3$, BL$_3$, S, Se, CH$_3$, SR, R, WL$_5$, CrL$_5$, MnL$_5$, MoL$_5$, ReL$_5$, PtL$_3$, PdL$_3$, CuL$_3$, CuL, RuL$_5$ IrL$_5$ FeL$_4$ RhL$_3$, RhL$_5$, CoL$_3$, NiL$_3$, AgL, AgL$_3$, or AuL where R or L is independently alkyl, alkenyl, alkynyl, alkylaryl, cycloalkyl, haloformyl, hydroxyl, aldehyde, carboxamide, amine, amino, alkoxy, azo, benzyl, carbonate ester, carboxylate, carboxyl, ketoamine, isocyanate, isocyanide, isothiocyanate, nitrile, nitro, nitroso, phosphine, phosphate, phosphono, pyridyl, sulfonyl, sulfo, sulfinyl, sulfhydryl, halo, aryl, substituted aryl, heteroaryl, substituted heteroaryl or a heterocyclic group;
- Y and Y' are independently selected from CR$^2$, S, SO$_2$, O, Se and NR', where R is an atom or group selected from the group of hydrogen atom, halogen atom, hydroxyl group, alkyl group, alkynyl group, alkoxy group, cyano group, nitro group, alkylcarbonyl group, alkoxycarbonyl group, perfluoroalkyl group, aryl group, cycloalkyl group, arylcarbonyl group, aryloxycarbonyl group, diarylamino group, dialkylamino group, mono- or dialkylaminocarbonyl group, alkylcaronyloxy group, arylcarbonyloxy group, aryloxy group, alkoxycarbonyl group, and aryloxycarbonyloxy group, and R$^4$ is a hydrogen atom or a substituted or unsubstituted alkyl, aryl or cycloalkyl group.

9. A method of making a photochromic compound comprising a diarylethene, in which an ethene moiety forms part of a mono- or poly-cyclic ring structure with at least one of a silicon-containing heterocycle or a phosphorus-containing heterocycle, comprising:
   a) performing an intermolecular coupling reaction of a 2-silylaryl bromide with an alkyne to provide the silicon-containing heterocycle comprising a photochromic diarylethene functional moiety, or
   b) performing an intramolecular dehydrogenative cyclization with a photochromic diarylethene functionalized intermediate to provide the phosphorus-containing heterocycle comprising a photochromic diarylethene functional moiety, or
   c) performing a silver-mediated dehydrogenative annulation with an alkyne to provide a phosphorus-containing heterocycle comprising a photochromic diarylethene functional moiety.

10. The method of claim 9, wherein a) is performed and the alkyne comprises 1,2-diarylethyne.

11. The method of claim 9, wherein b) is performed and the photochromic diarylethene functional moiety intermediate comprises cis-diarylethene-containing hydrophosphine oxide.

12. The method of claim 9, wherein c) is performed and the alkyne comprises 1,2-diarylethyne.

13. The method of claim 9, where b) is performed and the method further comprises functionalizing the phosphorus by one of:
   oxidation to phosphine oxides, sulfides or selenides;
   formation of phosphonium salts; or
   complexation with Lewis acids or transition metals.

14. The method of claim 9, where c) is performed and the method further comprises functionalizing the phosphorus by one of:
   oxidation to phosphine oxides, sulfides or selenides;
   formation of phosphonium salts; or
   complexation with Lewis acids or transition metals.

15. A photochromic device comprising a layer comprising the photochromic compound of claim 1 in a photochromic layer.

16. The photochromic device according to claim 15, wherein the layer comprising the photochromic compound is prepared by spin-coating, spray-coating, dip-coating, layer-by-layer deposition, or ink-jet printing, or vapor deposition.

17. The photochromic device according to claim 15, wherein the device is coated on a suitable substrate comprising quartz plate, glass plate or plastic film.

* * * * *